United States Patent [19]

Fabre et al.

[11] Patent Number: 4,529,728

[45] Date of Patent: Jul. 16, 1985

[54] 1H,3H-PYRROLO[1,2-C]THIAZOLE DERIVATIVES HAVING ANTI-ALLERGIC AND ANTI-INFLAMMATORY ACTIVITY

[75] Inventors: Jean-Louis Fabre, Paris; Daniel Farge, Thiais; Claude James; Daniel Lavé, both of Paris, all of France

[73] Assignee: Rhone-Poulenc Sante, Courbevoie, France

[21] Appl. No.: 569,908

[22] Filed: Jan. 11, 1984

[30] Foreign Application Priority Data

Jan. 13, 1983 [FR] France ................ 83 00453

[51] Int. Cl.³ .............. C07D 513/04; A61K 31/445
[52] U.S. Cl. ....................... 514/227; 544/124; 544/318; 544/336; 544/360; 546/193; 546/256; 546/270; 546/272; 546/274; 514/255; 514/256; 514/315; 514/277; 548/152; 548/171; 548/180
[58] Field of Search .............. 546/256, 270; 424/263, 424/250, 251, 267, 248.4; 548/152, 171; 544/124, 318, 336, 360

[56] References Cited

U.S. PATENT DOCUMENTS 3,544,590 12/1970 Kittleson .
3,865,839 2/1975 Allen et al. .

OTHER PUBLICATIONS

Robert, J. F., et al., Chem. Abstracts, 94:208760w.
Percy et al., Chemical Abstracts 75, 1971, 96775D.

Primary Examiner—Donald G. Daus
Assistant Examiner—S. A. Gibson
Attorney, Agent, or Firm—Stevens, Davis, Miller Mosher

[57] ABSTRACT

New compounds of the formula

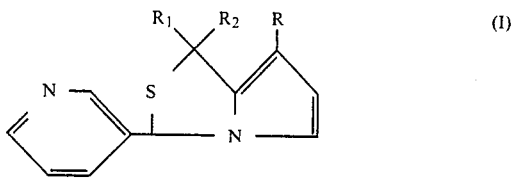

in which $R_1$ and $R_2$ = H or alkyl and (a) R = CN or alkylcarbonyl, or (b) R = CON($R_3$)$R_4$, in which $R_3$ = H and $R_4$ = NH$_2$, alkylamino, dialkylamino, phenylamino or diphenylamino; or $R_3$ and $R_4$ = H, alkyl (1 to 5 C) or substituted phenyl; or $R_3$ = H and $R_4$ = pyridyl or alkyl (1 to 5 C) substituted by COOH, NH$_2$, alkylamino, dialkylamino, morpholino, piperidino, pyrrolidin-1-yl, piperazin-1-yl (optionally substituted by alkyl, pyridyl or optionally substituted phenyl or benzyl), optionally substituted phenyl, pyridyl or imidazolyl; or $R_3$ and $R_4$ form an imidazolyl radical or a 5-membered or 6-membered heterocycle which can contain an oxygen, sulphur or nitrogen atom and which is optionally substituted by alkyl, alkoxycarbonyl, hydroxyalkyl, aminoalkyl, alkylaminoalkyl, dialkylaminoalkyl, pyridyl, pyrimidinyl, pyrazinyl, optionally substituted phenyl or optionally substituted benzyl; or (c) R = —C(=NOH)NH$_2$ or —C[=NN(R'R")NH$_2$], in which R' and R" = alkyl, the said alkyl radicals and alkyl portions being straight-chain or branched-chain and, unless mentioned otherwise, containing 1 to 4 carbon atoms, and the substituted phenyl and benzyl radicals carrying a halogen atom or an alkyl, alkoxy, alkylthio, trifluoromethyl or dialkylamino radical, and their tautomeric forms, addition salts with acids and the metals salts and the addition salts with nitrogen bases, are useful anti-allergic and anti-inflammatory agents. A variety of methods of making them are described.

16 Claims, No Drawings

1H,3H-PYRROLO[1,2-C]THIAZOLE DERIVATIVES HAVING ANTI-ALLERGIC AND ANTI-INFLAMMATORY ACTIVITY

The present invention provides 1H,3H-pyrrolo-[1,2-c]thiazole derivatives of the formula:

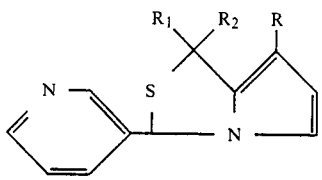

in which
R₁ and R₂, which are identical or different, represent a hydrogen atom or an alkyl radical and
(a) R represents a cyano or alkylcarbonyl radical, or
(b) R represents a radical of the formula:

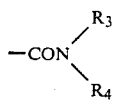

in which R₃ represents a hydrogen atom and R₄ represents an amino, alkylamino, dialkylamino, phenylamino or diphenylamino radical, or R₃ and R₄, which are identical or different, represent a hydrogen atom, an alkyl radical of 1 to 5 carbon atoms or an unsubstituted or substituted phenyl radical, or R₃ represents a hydrogen atom and R₄ represents a pyridyl radical or an alkyl radical of 1 to 5 carbon atoms, which is substituted by a carboxyl, amino, alkylamino, dialkylamino, morpholino, piperidino or pyrrolidin-1-yl radical, a piperazin-1-yl radical (unsubstituted or substituted in the 4-position by an alkyl radical, a pyridyl radical, an unsubstituted or substituted phenyl radical or an unsubstituted or substituted benzyl radical), an unsubstituted or substituted phenyl radical or a pyridyl or imidazolyl radical, or R₃ and R₄ together with the nitrogen to which they are attached form an imidazolyl radical or a 5-membered or 6-membered heterocycle which can also contain another heteroatom such as oxygen, sulphur or nitrogen and which is unsubstituted or substituted by an alkyl, alkoxycarbonyl, hydroxyalkyl, aminoalkyl, alkylaminoalkyl, dialkylaminoalkyl, pyridyl, pyrimidinyl or pyrazinyl radical, an unsubstituted or substituted phenyl radical or an unsubstituted or substituted benzyl radical, or
(c) R represents a radical of the formula:

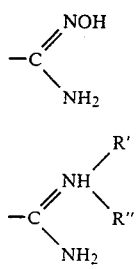

in which R' and R", which are identical or different, represent an alkyl radical, the alkyl radicals and alkyl portions in the aforesaid definitions being straight-chain or branched-chain and containing, unless mentioned or branched-chain and containing, unless mentioned otherwise, 1 to 4 carbon atoms each, the substituted phenyl and benzyl radicals, unless stated otherwise, carrying halogen, alkyl, alkoxy, alkylthio, trifluoromethyl or dialkylamino substituents, including the tautomeric forms of the said compounds when R represents a radical of the formula (III) or (IV), and the addition salts with acids and, where they exist, with metals and nitrogen bases.

According to the invention, the compounds of the formula (I) in which R represents a cyano radical and R₁ and R₂ are as defined above, i.e. the compounds of the formula:

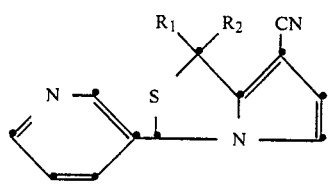

are prepared by reacting 2-chloroacrylonitrile of the formula:

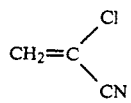

with a compound of the formula:

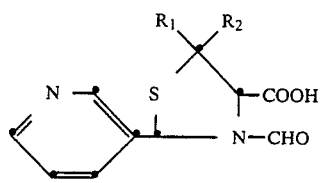

The reaction is generally carried out in acetic anhydride by heating to a temperature of between 80° and 130° C.

The compounds of the formula (VII) can be obtained by formylating the products of the general formula:

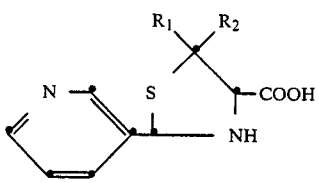

The formylation can advantageously be carried out by reaction with formic acid in acetic anhydride at a temperature of between 10° C. and 25° C.

The products of the general formula (VIII) can be prepared by the method of A. BANASHEK and M. I. SHCHUKINA, J. Gen. Chem. U.S.S.R. 31, 1374 (1961); Chem. Abstr. 55, 24739 h (1961).

According to the invention, the products of the general formula (I) in which R₁ and R₂ are defined as above and R represents a radical of the general formula (II) in which R₃ and R₄ together form an imidazolyl ring can be prepared by reacting N,N'-carbonyldiimidazole with an acid of the general formula:

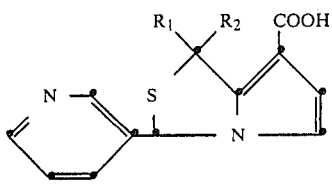

in which $R_1$ and $R_2$ are defined as above.

The reaction is generally carried out in an inert organic solvent such as tetrahydrofuran or dimethylformamide, at a temperature of the order of 20° C.

The products of the general formula (IX) can be prepared by hydrolysing the nitriles of the general formula (V) by any method known to those skilled in the art for converting a nitrile to an acid without affecting the rest of the molecule, in particular by heating in an alkaline medium in a high-boiling alcohol such as ethylene glycol, at a temperature of between 100° C. and the reflux temperature of the reaction mixture.

According to the invention, the products of the general formula (I) in which $R_1$ and $R_2$ are defined as above and R represents a radical of the general formula (II) in which $R_3$ and $R_4$ are defined as under (b), except that $R_3$ and $R_4$ cannot together form an imidazolyl ring, can be prepared by reacting ammonia or a product of the general formula:

in which $R_3$ and $R_4$ are defined as above under (b), except that $R_3$ and $R_4$ cannot together form an imidazolyl ring, with an acid of the general formula (IX).

If $R_3$ or $R_4$ represents an alkyl radical containing 1 to 5 carbon atoms, which is substituted by an amino, alkylamino or piperazinyl radical, or alternatively if $R_3$ and $R_4$ together form, with the nitrogen atom to which they are bonded, a 5-membered or 6-membered heterocycle containing another nitrogen atom and optionally substituted by an aminoalkyl radical, the corresponding amine groups must be protected prior to condensation with the acid of the general formula (IX).

The blocking and subsequent unblocking can be carried out by any method known to those skilled in the art for protecting a primary or secondary amine group, e.g. in the form of the trifluoroacetamide, the unblocking being carried out using ammoniacal methanol.

It is particularly advantageous to use the acid of the general formula (IX) in an activated form, e.g.:

(α) in the form of the acid chloride; in this case, the reaction is carried out in a halogenated solvent such as chloroform, methylene chloride or 1,2-dichloroethane, or an ether such as dioxane, at a temperature of between 20° C. and the reflux temperature of the reaction mixture, or (β) in the form of a mixed anhydride obtained by reacting an alkyl chloroformate with the acid of the general formula (IX); in this case, the reaction is carried out in a solvent such as ether or tetrahydrofuran, or alternatively in dimethylformamide, at a temperature of between 20° C. and the reflux temperature of the reaction mixture, or (γ) in the form of an imidazolide, i.e. a product of the general formula (I) in which $R_1$ and $R_2$ are defined as above and R represents a radical of the general formula (II) in which $R_3$ and $R_4$ together form an imidazolyl ring; in this case, the reaction is carried out in an organic solvent such as tetrahydrofuran or dimethylformamide, or a mixture of these solvents, at a temperature of between 20° C. and the reflux temperature of the reaction mixture.

According to the invention, the products of the general formula (I) in which $R_1$ and $R_2$ are defined as above and R represents a radical of the general formula (II) in which $R_3$ and $R_4$ each represent a hydrogen atom can also be prepared by hydrolysing a nitrile of the general formula (V). The hydrolysis can be carried out by any method known to those skilled in the art for converting a nitrile to an amide without affecting the rest of the molecule, in particular by heating in an alkaline medium in an organic solvent such as tert.-butanol.

According to the invention, the products of the general formula (I) in which $R_1$ and $R_2$ are defined as above and R represents a radical of the general formula (II) in which $R_3$ and $R_4$ each represent a hydrogen atom can also be prepared by reacting 2-chloroacrylamide of the formula:

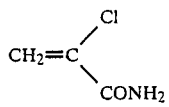

with an acid of the general formula (VII) in which $R_1$ and $R_2$ are defined as above.

The reaction is generally carried out in acetic anhydride by heating to a temperature of between 80° C. and 130° C.

According to the invention, the products of the general formula (I) in which $R_1$ and $R_2$ are defined as above and R represents an acetyl radical can be prepared by reacting the ethoxymagnesium derivative of ethyl malonate with a product of the general formula:

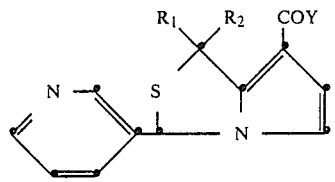

in which $R_1$ and $R_2$ are defined as above and Y represents a halogen atom, and then hydrolysing and decarboxylating the product obtained.

The reaction is generally carried out in an organic solvent such as an ether or an alcohol, or a mixture of these solvents, in the presence of an acid acceptor such as triethylamine, at a temperature of between 10° C. and the reflux temperature of the reaction mixture, the hydrolysis and decarboxylation being carried out by the methods known to those skilled in the art.

The products of the general formula (XII) can be prepared from the acids of the general formula (IX) by any method known to those skilled in the art for converting an acid to an acid halide.

According to the invention, the products of the general formula (I) in which $R_1$ and $R_2$ are defined as above and R represents an alkylcarbonyl radical can be prepared by reacting an organomagnesium derivative of the general formula:

$$R'''MgX \qquad (XIII)$$

in which R''' represents an alkyl radical and X represents a halogen atom, with a nitrile of the general formula (V), this being followed by hydrolysis.

The reaction is carried out by any method known to those skilled in the art for obtaining a ketone from a nitrile and an organomagnesium derivative without affecting the rest of the molecule.

According to the invention, the products of the general formula (I) in which $R_1$ and $R_2$ are defined as above and R represents a radical of the general formula (IV), defined as above, can be prepared by reacting a hydrazine of the general formula:

$$H_2N-N\begin{array}{c}R'\\R''\end{array} \qquad (XIV)$$

in which R' and R'' represent identical or different alkyl radicals, with a product of the general formula:

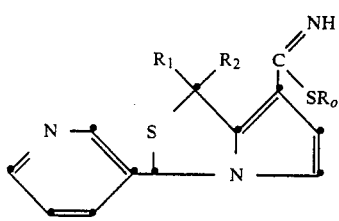

(XV)

in which $R_o$ represents an alkyl radical and $R_1$ and $R_2$ are defined as above.

The reaction is generally carried out in an organic solvent such as ethanol, at a temperature of between 20° C. and 80° C.

The products of the general formula (XV) can be obtained by reacting an alkyl halide of the general formula:

$$R_o-Z \qquad (XVI)$$

in which $R_o$ represents an alkyl radical and Z represents a halogen atom, preferably an iodine atom, with a product of the general formula:

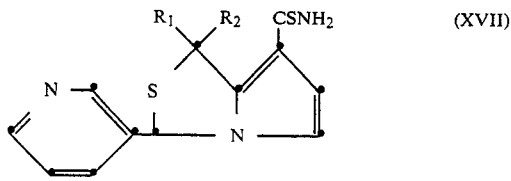

(XVII)

in which $R_1$ and $R_2$ are defined as above.

The reaction is generally carried out in an organic solvent such as acetone or dimethylformamide, or a mixture of these solvents, at a temperature of between 0° C. and 50° C.

The products of the general formula (XVII) can be prepared by thionating a product of the general formula (I) in which $R_1$ and $R_2$ are defined as above and R represents a radical of the general formula (II) in which $R_3$ and $R_4$ represent a hydrogen atom.

The reaction is generally carried out by means of a thionating reagent, e.g. by means of LAWESSON's reagent [2,4-bis-(4-methoxyphenyl)-1,3,2,4-dithiadiphosphetane-2,4-dithione], in an organic solvent such as toluene at a temperature of the order of 50° C., or such as 1,2-dimethoxyethane or hexamethylphosphoramide at a temperature of the order of 20° C., or alternatively by means of phosphorus pentasulphide in an organic solvent such as toluene or dioxane or, preferably, in a solvent such as pyridine, in the presence of a stream of hydrogen sulphide.

According to the invention, the products of the general formula (I) in which $R_1$ and $R_2$ are defined as above and R represents a radical of the formula (III) can be prepared by reacting hydroxylamine with a product of the general formula (XVII).

Hydroxylamine hydrochloride is generally employed and the reaction is carried out in an organic solvent such as pyridine, in the presence of mercuric chloride, at a temperature of the order of 20° C.

The new products of the general formula (I) can be purified by the usual known methods, e.g. crystallisation, chromatography or successive extractions in acid and basic media.

The new products of the general formula (I) can be converted to addition salts with acids by reaction with an acid in an organic solvent such as an alcohol, a ketone, an ether or a chlorinated solvent. The salt formed precipitates, if necessary after concentration of its solution; it is separated off by filtration or decantation.

The new products of the general formula (I) in which R represents a radical of the general formula (II) in which $R_3$ represents a hydrogen atom and $R_4$ represents an alkyl radical containing 1 to 5 carbon atoms, which is substituted by a carboxyl radical, can be converted to metal salts or to addition salts with nitrogen bases by any method known to those skilled in the art for carrying out this conversion without affecting the rest of the molecule.

Compounds of formula I and their addition salts have valuable pharmacological properties coupled with a low toxicity. They have been shown to be active at concentrations of less than 50 mg/liter in the test for measuring the in vitro inhibitory activity towards platelet aggregation caused by 1-0-octadecyl 2-0-acetyl ns-glycero-3-phosphorylcholine (P.A.F.-Acether using the technique of G.V.R. BORN et al. J. Physiol. 168, 178 (1963). Their toxic dose (expressed by the $LD_{50}$) in mice is generally between 300 and 900 mg/kg, when administered orally.

Of particular value are the compounds of formula (I) in which $R_1$ and $R_2$ both represent a hydrogen atom or an alkyl radical and (a) R represents a cyano or alkylcarbonyl radical, or
(b) R represents a radical of the formula (II) in which $R_3$ represents a hydrogen atom and $R_4$ represents an amino radical, or $R_3$ and $R_4$, which are identical or different, represent a hydrogen atom or a pyridyl radical, an alkyl radical or a phenyl radical which is unsubstituted or substituted by halogen, alkyl, alkoxy or dimethylamino, or $R_3$ represents a hydrogen atom and $R_4$ represents alkyl of 1 to 5 carbon atoms, which is substituted by a carboxyl, dialkylamino or piperidino radical, a piperazin-1-yl radical (substituted in the 4-position by a pyridyl radical) or a phenyl or imidazolyl radical, or $R_3$ and $R_4$ together with the nitrogen to which they are attached form an imidazolyl ring or a piperazinyl ring substituted in the 4-position by a hydroxyalkyl, pyridyl or pyrimidyl radical, a phenyl radical (unsubstituted or substituted by an alkoxy radical) or a benzyl radical, or (c) R represents a radical of the formula (III) or (IV) in which R' and R", which are identical, represent an alkyl radical.

Of more particular value are the compounds of the formula (I) in which $R_1$ and $R_2$ represent a hydrogen atom and R represents a radical of the formula (II) in which $R_3$ and $R_4$, which are identical or different, represent a hydrogen atom or an alkyl or phenyl radical, or $R_3$ represents a hydrogen atom and $R_4$ represents a pyridyl radical or an alkyl radical substituted by a phenyl or imidazolyl radical, or $R_3$ and $R_4$ together form a piperazinyl ring substituted in the 4-position by a pyridyl, phenyl or benzyl radical.

The following compounds are of especial value:

N-Pyridin-2-yl-3-(pyridin-3-yl)-1H,3H-pyrrolo[1,2-c]thiazole-7-carboxamide,

N-Phenyl-3-(pyridin-3-yl)-1H,3H-pyrrolo[1,2-c]thiazole-7-carboxamide, 3-(Pyridin-3-yl)-1H,3H-pyrrolo[1,2-c]thiazole-7-carboxamide, N-Pyridin-3-yl-3-(pyridin-3-yl)-1H,3H-pyrrolo[1,2-c]thiazole-7-carboxamide, N-Methyl-3-(pyridin-3-yl)-1H,3H-pyrrolo[1,2-c]thiazole-7-carboxamide, N-Butyl-3-(pyridin-3-yl)-1H,3H-pyrrolo[1,2-c]thiazole-7-carboxamide, N-Benzyl-3-(pyridin-3-yl)-1H,3H-pyrrolo[1,2-c]thiazole-7-carboxamide, N- [2-(Imidazol-4-yl)- ethyl]3-(pyridin-3-yl)-1H,3H-pyrrolo[1,2-c]thiazole-7-carboxamide, (4-Phenylpiperazin-1-yl)-7-carbonyl-3-(pyridin-3-yl)-1H,3H-pyrrolo[1,2-c]thiazole,

[4-Pyridin-2-yl)-piperazin-1-yl]-7-carbonyl-3-(pyridin-3-yl)-1H,3H-pyrrolo[1,2-c]thiazole, and (4-Benzylpiperazin-1-yl)-7-carbonyl-3-(pyridin-3-yl)-1H,3H-pyrrolo[1,2-c]thiazole.

For use in therapy, the compounds of formula (I) can be employed as such or, if appropriate, in the form of pharmaceutically acceptable salts, i.e. salts which are non-toxic at the dosages used.

Pharmaceutically acceptable salts which may be mentioned are the addition salts with mineral acids, such as the hydrochlorides, sulphates, nitrates and phosphates, or with organic acids, such as the acetates, propionates, succinates, benzoates, fumarates, maleates, methanesulphonates, isethionates, theophyllineacetates, salicylates, phenolphthaleinates and methylene-bis-$\beta$-oxynaphthoates or substitution derivatives of these compounds.

The Examples which follow illustrate the invention.

EXAMPLE 1

A mixture of 3-formyl-2-(pyridin-3-yl)-thiazolidine-4-carboxylic acid (249.4 g), 2-chloroacrylonitrile (457 g) and hydroquinone (0.2 g) in acetic anhydride (1760 cc) is heated at a temperature of between 110° C. and 117° C. for 70 minutes. The solvent is then evaporated off under reduced pressure (20 mm Hg; 2.7 kPa) at a temperature of between 50° C. and 80° C. The residue is taken up in distilled water (400 cc); the suspension obtained is brought to a pH of the order of 10 by adding a 5N aqueous solution of sodium hydroxide and then extracted 4 times with methylene chloride (2500 cc in total). The organic extracts are combined, washed 3 times with distilled water (1500 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. The residue obtained is dissolved in a mixture of ethyl acetate (250 cc) and a 1.8N aqueous solution of hydrochloric acid (500 cc). The organic phase is separated off by decantation and extracted twice with distilled water (200 cc in total). The aqueous extracts are combined, washed 5 times with ethyl acetate (500 cc in total), treated with decolourising charcoal (0.5 g) and filtered; the filtrate is brought to a pH of the order of 10 by adding a 10N aqueous solution of sodium hydroxide at a temperature of the order of 4° C. and then extracted 3 times with ethyl acetate (650 cc in total). The organic extracts are combined, washed 3 times with distilled water (450 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a crude product (71.2 g). This product is dissolved in boiling propan-2-ol (150 cc) and the solution obtained is treated with decolourising charcoal (0.5 g) and then filtered hot; the filtrate is cooled at a temperature of the order of 4° C. for 1 hour. The crystals which have appeared are filtered off, washed 3 times with propan-2-ol cooled to a temperature of the order of 4° C. (30 cc in total) and 3 times with isopropyl ether (60 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carbonitrile (44 g) in the form of ochre-coloured crystals melting at 117° C.

The 3-formyl-2-(pyridin-3-yl)-thiazolidine-4-carboxylic acid can be obtained in the following manner:

2-(Pyridin-3-yl)-thiazolidine-4-carboxylic acid (250 g) is added to formic acid (1200 cc), the temperature of the reaction medium being kept below 25° C. Acetic anhydride (875 g) is added to the solution thus obtained in the course of 1 hour, the temperature being kept at between 10° C. and 18° C.

After stirring for 20 hours at a temperature of the order of 20° C., the solvent is evaporated off under reduced pressure (20 mm Hg; 2.7 kPa) at a temperature of the order of 60° C., the residue is taken up in ethanol (1000 cc) and the mixture is heated at the boil for 5 minutes and then cooled at a temperature of the order of 4° C. for 1 hour; the crystals which have appeared are filtered off, washed 3 times with ethanol (600 cc in total) and then 3 times with diethyl ether (300 cc in total) and dried under reduced pressure (20 mm Hg; 2.7 kPa) at a temperature of the order of 20° C., in the presence of potassium hydroxide pellets. This gives 3-formyl-2-(pyridin-3-yl)-thiazolidine-4-carboxylic acid (234.5 g) in the form of cream crystals melting at 214° C.

The 2-(pyridin-3-yl)-thiazolidine-4-carboxylic acid can be prepared according to A BANASHEK and M. I. SHCHUKINA, J. Gen. Chem. U.S.S.R., 31, 1374 (1961); Chem. Abstr. 55, 24739 h (1961).

EXAMPLE 2

A solution of 2-diethylaminoethylamine (9.5 g) in anhydrous tetrahydrofuran (50 cc) is added in the course of 10 minutes, at a temperature of the order of 25° C., to a solution of 3-(pyridin-3-yl)-1H,3H-pyrrolo[1,2-c]thiazole-7-carboxylic acid (10.2 g) and N,N'-carbonyldiimidazole (10.1 g) in anhydrous tetrahydrofuran (150 cc), stirred under dry nitrogen at a temperature of the order of 20° C. for 1 hour 20 minutes. After stirring for one hour at a temperature of the order of 20° C., the solvent is evaporated off under reduced pressure (20 mm Hg; 2.7 kPa) at a temperature of the order of 40° C. The residue obtained is taken up in distilled water (700 cc) and the mixture is extracted 5 times with ethyl acetate (750 cc in total). The organic extracts are combined, washed 5 times with distilled water (500 cc) in total, dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a crude product (12.4 g). This product, combined with the product prepared in the same manner in another earlier operation (2 g) is dissolved in a boiling mixture of cyclohexane and ethyl acetate (50/50 by volume) (100 cc). The solution obtained is treated with decolourising charcoal (0.5 g) and then filtered hot; the filtrate is cooled at a temperature of the order of 4° C. for 2 hours. The crystals which have appeared are filtered off, washed 3 times with isopropyl ether (45 cc in total) and dried under reduced pressure (20 mm Hg; 2.7 kPa) at a temperature of the order of 20° C., in the presence of potassium hydroxide pellets. This gives N-(2-diethylaminoethyl)-3-(pyridin-3-yl)-1H,3H-pyrrolo[1,2-c]thiazole-7-carboxamide (9.8 g) in the form of white crystals melting at 129° C.

The 3-(pyridin-3-yl)-1H,3H-pyrrolo[1,2-c]thiazole-7-carboxylic acid can be obtained in the following manner:

3-(Pyridin-3-yl)-1H,3H-pyrrolo[1,2-c]thiazole-7-carbonitrile (48 g) is added to a solution of potassium hydroxide pellets (41.7 g) in ethylene glycol (400 cc). The reaction mixture is heated at a temperature of the order of 150° C. for 6 hours 30 minutes. After stirring for 16 hours at a temperature of the order of 20° C., the solvent is evaporated off under reduced pressure (5 mm Hg; 0.7 kPa) at a temperature of the order of 100° C. The residue is dissolved in distilled water (380 cc). The solution obtained is treated with decolourising charcoal (0.5 g) and filtered, and the filtrate is brought to a pH of the order of 4 by adding a concentrated aqueous solution of hydrochloric acid, the temperature being kept at about 20° C. The crystals which have appeared are filtered off, washed 3 times with distilled water (600 cc in total) and then dried under reduced pressure (20 mm Hg; 2.7 kPa) at a temperature of the order of 20° C., in the presence of potassium hydroxide pellets. This gives a crude product (49.5 g) melting at 177° C. This product is dissolved in boiling ethanol (840 cc). The solution obtained is treated with decolourising charcoal (0.5 g) and then filtered hot; the filtrate is cooled at a temperature of the order of 4° C. for 1 hour. The crystals which have appeared are filtered off, washed 3 times with ethanol cooled to a temperature of the order of 4° C. (45 cc in total) and then 3 times with diethyl ether (90 cc in total) and dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carboxylic acid (36.6 g) in the form of cream crystals melting at 178° C.

EXAMPLE 3

A mixture of 3-(pyridin-3-yl)-1H,3H-pyrrolo[1,2-c]thiazole-7-carbonitrile (13.6 g) and powdered potassium hydroxide (21 g) in tert.-butyl alcohol (150 cc) is heated for 3 hours 15 minutes at a temperature of the order of 85° C., with stirring. The solvent is then evaporated off under reduced pressure (20 mm Hg; 2.7 kPa) at a temperature of the order of 40° C., the residue is then resuspended in distilled water (500 cc) and the suspension is stirred for 5 minutes at a temperature of the order of 20° C.; the crystals which have appeared are filtered off, washed 5 times with distilled water (500 cc in total), 3 times with ethanol (60 cc in total) and then 3 times with diethyl ether (60 cc in total) and dried under reduced pressure (20 mm Hg; 2.7 kPa) at a temperature of the order of 20° C., in the presence of potassium hydroxide pellets. This gives a crude product (12.1 g) melting at 208° C. This product, combined with the product prepared in the same manner in another earlier operation (2.2 g), is dissolved in boiling ethanol (800 cc). The solution obtained is treated with decolourising charcoal (0.5 g) and then filtered hot. The filtrate is cooled for 1 hour at a temperature of the order of 4° C.; the crystals which have appeared are filtered off, washed 3 times with ethanol cooled to a temperature of the order of 4° C. (30 cc in total) and dried under reduced pressure (20 mm Hg; 2.7 kPa) at a temperature of the order of 20° C., in the presence of potassium hytdroxide pellets. This gives 3-(pyridin-3-yl)-1H,3H-pyrrolo[1,2-c]thiazole-7-carboxamide (10.7 g) in the form of white crystals melting at 210° C.

The 3-(pyridin-3-yl)-1H,3H-pyrrolo[1,2-c]thiazole-7-carbonitrile is prepared as in Example 1.

EXAMPLE 4

A solution of 3-(pyridin-3-yl)-1H,3H-pyrrolo[1,2-c]thiazole-7-carboxylic acid (6.15 g) and N,N'-carbonyldiimidazole (4.45 g) in anhydrous tetrahydrofuran (50 cc) is stirred under dry nitrogen at a temperature of the order of 20° C. for 1 hour. A solution of N-(2-aminoethyl)-piperidine (3.87 g) in anhydrous tetrahydrofuran (10 cc) is added to the solution thus obtained in the course of 20 minutes, at a temperature of the order of 25° C. After stirring for 16 hours at a temperature of the order of 20° C., distilled water (25 cc) is added to the reaction medium and the solvent is evaporated off under reduced pressure (20 mm Hg; 2.7 kPa) at a temperature of the order of 40° C. The residue is dissolved in ethyl acetate (300 cc) and the solution thus obtained is washed 5 times with distilled water (400 cc in total), dried over anhydrous magnesium sulphate, treated with decolourising charcoal (0.2 g) and filtered, and the filtrate is concentrated to dryness under reduced pressure (20 mm Hg; 2.7 kPa) at a temperature of the order of 40° C. The residue is dissolved in a 0.4 N aqueous solution of hydrochloric acid (100 cc) and the solution obtained is extracted 3 times with methylene chloride (120 cc in total) and then treated with decolourising charcoal (0.2 g) and filtered. The filtrate is brought to a pH of the order of 10 by adding a 10 N aqueous solution of sodium hydroxide and is extracted 5 times with ethyl acetate (400 cc in total). The organic extracts are combined, washed 5 times with distilled water (400 cc in total), dried over anhydrous magnesium sulphate, treated with decolourising charcoal (0.2 g) and filtered, and the filtrate is concentrated to dryness under reduced pressure (20 mm Hg; 2.7 kPa) at a temperature of the order of 40°

C. This gives a crude product (7.6 g). This product is dissolved in boiling acetonitrile (80 cc) and the solution is treated with decolourising charcoal (0.2. g) and then filtered hot; the filtrate is cooled at a temperature of the order of 4° C. for 16 hours. The crystals which have appeared are filtered off, washed 3 times with acetonitrile cooled to a temperature of the order of 4° C. (20 cc in total) and dried under reduced pressure (20 mm Hg; 2.7 kPa) at a temperature of the order of 20° C., in the presence of potassium hydroxide pellets. This gives N-(2-piperidinoethyl)-3-(pyridin-3-yl)-1H,3H-pyrrolo[1,2-c]thiazole-7-carboxamide (5.9 g) in the form of white crystals melting at 150° C.

The 3-(pyridin-3-yl)-1H,3H-pyrrolo[1,2-c]thiazole-7-carboxylic acid is prepared as in Example 2.

EXAMPLE 5

A solution of 3-(pyridin-3-yl)-1H,3H-pyrrolo[1,2-c]thiazole-7-carboxylic acid (7.6 g) and N,N'-carbonyldiimidazole (6.9 g) in anhydrous tetrahydrofuran (25 cc) is stirred under dry nitrogen at a temperature of the order of 20° C. for 1 hour 20 minutes. 2-Dimethylaminoethylamine (5.4 g), diluted in anhydrous tetrahydrofuran (30 cc), is added to the solution thus obtained in the course of 10 minutes at a temperature of the order of 25° C. After stirring for 16 hours at a temperature of the order of 20° C., distilled water (20 cc) is added to the reaction mixture and the solvent is evaporated off under reduced pressure (20 mm Hg; 2.7 kPa) at a temperature of the order of 40° C. The residue is dissolved in ethyl acetate (350 cc) and the solution thus obtained is washed 5 times with distilled water (400 cc in total), dried over anhydrous magnesium sulphate, treated with decolourising charcoal (0.2 g) and filtered, and the filtrate is concentrated to dryness under reduced pressure (20 mm Hg; 2.7 kPa) at a temperature of the order of 40° C. This gives a crude product (6.2 g). This product is chromatographed on a column of diameter 2.5 cm, containing silica (0.063–0.2 mm) (60 g). Elution is carried out with a mixture of ethyl acetate and methanol (50/50 by volume), 100 cc fractions being collected. The first fraction is discarded; the next 9 fractions are combined and concentrated to dryness under reduced pressure (20 mm Hg; 2.7 kPa) at a temperature of the order of 20° C. This gives a product (5.6 g), which is redissolved in boiling acetonitrile (60 cc). The solution obtained is treated with decolourising charcoal (0.2 g) and filtered hot; the filtrate is cooled at a temperature of the order of 4° C. for 1 hour. The crystals which have appeared are filtered off, washed 3 times with acetonitrile cooled to a temperature of the order of 4° C. (10 cc in total) and dried under reduced pressure (20 mm Hg; 2.7 kPa) at a temperature of the order of 20° C., in the presence of potassium hydroxide pellets. This gives N-(2-dimethylaminoethyl)-3-(pyridin-3-yl)-1H,3H-pyrrolo[1,2-c]thiazole-7-carboxamide (2.3 g) in the form of cream crystals melting at 150° C.

The 3-(pyridin-3-yl)-1H,3H-pyrrolo[1,2-c]thiazole-7-carboxylic acid is prepared as in Example 2.

EXAMPLE 6

A solution of 3-(pyridin-3-yl)-1H,3H-pyrrolo[1,2-c]thiazole-7-carboxylic acid (7.4 g) and N,N'-carbonylidiimidazole (5.35 g) in anhydrous tetrahydrofuran (50 cc) is stirred under dry nitrogen at a temperature of the order of 20° C. for 2 hours 20 minutes. The solution obtained is saturated with a stream of anhydrous monomethylamine, the temperature of the reaction mixture being kept at about 20° C. for 1 hour 30 minutes. After stirring for 16 hours at a temperature of the order of 20° C., the reaction mixture is treated with distilled water (500 cc) and cooled for 30 minutes at a temperature of the order of 4° C.; the crystals which have appeared are filtered off, washed 3 times with distilled water (150 cc in total) and dried under reduced pressure (20 mm Hg; 2.7 kPa) at a temperature of the order of 20° C., in the presence of potassium hydroxide pellets. This gives a crude product (5.5 g) melting at 168° C. This product is dissolved in boiling acetonitrile (65 cc). The solution is treated with decolourising charcoal (0.5 g) and filtered hot; the filtrate is cooled at a temperature of the order of 4° C. for 30 minutes. The crystals which have appeared are filtered off, washed 3 times with acetonitrile cooled to a temperature of the order of 4° C. (10 cc in total) and dried under reduced pressure (20 mm Hg; 2.7 kPa) at a temperature of the order of 20° C., in the presence of potassium hydroxide pellets. This gives N-methyl-3-(pyridin-3-yl)-1H,3H-pyrrolo[1,2-c]thiazole-7-caboxamide (4.3 g) in the form of white crystals melting at 179° C.

The 3-(pyridin-3-yl)-1H,3H-pyrrolo[1,2-c]thiazole-7-carboxylic acid is prepared as in Example 2.

EXAMPLE 7

A solution of 3-(pyridin-3-yl)-1H,3H-pyrrolo[1,2-c]thiazole-7-carboxylic acid (7.4 g) and N,N'-carbonyldiimidazole (7.3 g) in anhydrous tetrahydrofuran (50 cc) is stirred under dry nitrogen at a temperature of the order of 20° C. for 4 hours. The solution obtained is saturated for 2 hours, at a temperature of the order of 10° C., with a stream of anhydrous dimethylamine. After stirring for 16 hours at a temperature of the order of 20° C., the reaction medium is treated with distilled water (30 cc) at a temperature of between 21° C. and 29° C. and the solvent is then evaporated off under reduced pressure (20 mm Hg; 2.7 kPa) at a temperature of the order of 40° C. The residue is dissolved in methylene chloride (250 cc) and the solution obtained is washed 5 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a crude product (7.5 g). This product is chromatographed on a column of diameter 5 cm, containing silica (0.040–0.063 mm) (400 g). Elution is carried out with a mixture of methylene chloride and methanol (95/5 by volume) under a pressure of 0.5 bar (51 kPa), 75 cc fractions being collected. The first 4 fractions are discarded; the next 10 fractions are combined and concentrated to dryness under reduced pressure (20 mm Hg; 2.7 kPa) at a temperature of the order of 40° C. This gives a product (6.8 g). This product is dissolved in boiling acetonitrile (30 cc). The solution is treated with decolourising charcoal (0.5 g) and filtered hot; the filtrate is cooled at a temperature of the order of 4° C. for 1 hour. The crystals which have appeared are filtered off, washed 3 times with acetonitrile cooled to a temperature of the order of 4° C. (10 cc in total) and dried under reduced pressure (20 mm Hg; 2.7 kPa) at a temperature of the order of 20° C., in the presence of potassium hydroxide pellets. This gives N,N-dimethyl-3-(pyridin-3-yl)-1H,3H-pyrrolo[1,2-c]thiazole-7-carboxamide (4.4 g) in the form of cream crystals melting at 129° C.

The 3-(pyridin-3-yl)-1H,3H-pyrrolo[1,2-c]thiazole-7-carboxylic acid is prepared as in Example 2.

EXAMPLE 8

A mixture of 1,1-dimethyl-3-(pyridin-3-yl)-1H,3H-pyrrolo[1,2-c]thiazole-7-carbonitrile (9.9g) and powdered potassium hydroxide (13.6 g) in tert.-butyl alcohol (140 cc) is heated for 7 hours 20 minutes at a temperature of the order of 84° C., with stirring. After stirring for 16 hours at a temperature of the order of 20° C., the reaction mixture is heated for a further 3 hours 30 minutes at a temperature of the order of 85° C., with stirring. The solvent is evaporated off under reduced pressure (20 mm Hg; 2.7 kPa) at a temperature of the order of 40° C. The residue is suspended in distilled water (300 cc) and the suspension is stirred for 15 minutes at a temperature of the order of 4° C.; the crystals which have appeared are filtered off, washed 3 times with distilled water (300 cc in total) and dried under reduced pressure (20 mm Hg; 2.7 kPa) at a temperature of the order of 20° C., in the presence of potassium hydroxide pellets. This gives a crude product (10.5 g). This product is dissolved in boiling ethyl acetate (65 cc) and the solution obtained is treated with decolourising charcoal (0.5 g) and filtered hot; the filtrate is cooled at a temperature of the order of 4° C. for 1 hour. The crystals which have appeared are filtered off, washed 3 times with ethyl acetate cooled to a temperature of the order of 4° C. (10 cc in total) and dried under reduced pressure (20 mm Hg; 2.7 kPa) at a temperature of the order of 20° C., in the presence of potassium hydroxide pellets. This gives 1,1-dimethyl-3-(pyridin-3-yl)-1H,3H-pyrrolo[1,2-c]thiazole-7-carboxamide (9 g) in the form of white crystals melting at 140° C.

The 1,1-dimethyl-3-(pyridin-3-yl)-1H,3H-pyrrolo[1,2-c]thiazole-7-carbonitrile can be prepared in the following manner:

2-Chloroacrylonitrile (117 g) is added, at a temperature of the order of 80° C., to a solution of 5,5-dimethyl-3-formyl-2-(pyridin-3-yl)-thiazolidine-4-carboxylic acid (71.4 g) and hydroquinone (0.5 g) in acetic anhydride (450 cc). After stirring for 1 hour 30 minutes at a temperature of the order of 110° C., the reaction mixture is concentrated to dryness under reduced pressure (20 mm Hg; 2.7 kPa) at a temperature of between 50° C. and 80° C. The residue is taken up in distilled water cooled to a temperature of the order of 0° C. (200 cc); the suspension obtained is brought to a pH of the order of 10 by adding a 2 N aqueous solution of sodium hydroxide and then extracted 3 times with ethyl acetate (800 cc in total). The organic extracts are combined, washed 5 times with distilled water (750 cc in total), dried over anhydrous magnesium sulphate, treated with decolourising charcoal (0.5 g) and filtered, and the filtrate is concentrated to dryness under reduced pressure (20 mm Hg, 2.7 kPa) at a temperature of the order of 40° C. The residue is taken up in a 2 N aqueous solution of hydrochloric acid (200 cc) and the suspension is extracted with ethyl acetate (200 cc) for 10 minutes, with stirring. The organic phase is separated off and re-extracted twice with a 2 N aqueous solution of hydrochloric acid (100 cc in total). The aqueous extracts are combined, treated with decolourising charcoal (0.5 g) and filtered, and the filtrate is cooled to a temperature of the order of 4° C. and brought to a pH of the order of 10 by adding a 10 N aqueous solution of sodium hydroxide. Extraction is then carried out 6 times with ethyl acetate (900 cc in total). The organic extracts are combined, washed 5 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a crude product (29.4 g). This product is chromatographed on a column of diameter 4.5 cm, containing silica (0.063-0.2 mm) (290 g), 500 cc fractions being collected. The first 4 fractions from elution with a mixture of cyclohexane and ethyl acetate (80/20 by volume) are discarded. The fifth fraction from elution with a mixture of cyclohexane and ethyl acetate (80/20 by volume), the next 7 fractions from elution with a mixture of cyclohexane and ethyl acetate (75/25 by volume) and the next 4 fractions from elution with a mixture of cyclohexane and ethyl acetate (70/30 by volume) are combined and concentrated to dryness under reduced pressure (20 mm Hg; 2.7 kPa) at a temperature of the order of 40° C. This gives a crystalline product (25.8 g). This product is suspended in isopropyl ether (150 cc). The crystals are filtered off, washed 3 times with isopropyl ether (150 cc in total) and dried-under reduced pressure (20 mm Hg; 2.7 kPa) at a temperature of the order of 20° C., in the presence of potassium hydroxide pellets. This gives a product (20 g) melting at 111° C.

This product is chromatographed on a column of diameter 6 cm, containing silica (0.04-0.063 mm) (480 g). Elution is carried out with a mixture of cyclohexane and ethyl acetate (55/45 by volume) under a pressure of 0.5 bar (51 kPa), 500 cc fractions being collected. The first 3 fractions are discarded and the next 6 fractions are combined and concentrated to dryness under reduced pressure (20 mm Hg; 2.7 kPa) at a temperature of the order of 40° C. This gives 1,1-dimethyl-3-(pyridin-3-yl)-1H,3H-pyrrolo[1,2-c]thiazole-7-carbonitrile (19.8 g) in the form of white crystals melting at 112° C.

The 5,5-dimethyl-3-formyl-2-(pyridin-3-yl)-thiazolidine-4-carboxylic acid can be obtained in the following manner:

Acetic anhydride (302 g) is added in the course of 45 minutes, at a temperature of between 8° C. and 15° C., to a solution of 5,5-dimethyl-2-(pyridin-3-yl)-thiazolidine-4-carboxylic acid (91 g) in formic acid (420 cc). After stirring for 16 hours at a temperature of the order of 20° C., distlled water (65 cc) is added to the reaction medium and the solvent is evaporated off under reduced pressure (20 mm Hg; 2.7 kPa) at a temperature of the order of 60° C. The residue is taken up in ethanol (250 cc) and the solvent is evaporated off under reduced pressure (20 mm Hg; 2.7 kPa) at a temperature of the order of 60°C. This gives a crude product (115 g). This product is taken up in boiling ethanol (250 cc). After cooling to a temperature of the order of 4° C., the crystals are filtered off, washed 3 times with ethanol cooled to a temperature of the order of 4° C. (60 cc in total) and then 3 times with diethyl ether (150 cc in total) and dried under reduced pressure (20 mm Hg; 2.7 kPa) at a temperature of the order of 20° C., in the presence of potassium hydroxide pellets. This gives 5,5-dimethyl-3-formyl-2-(pyridin-3-yl)-thiazolidine-4-carboxylic acid (71.6 g) in the form of white crystals melting at 185° C.

The 5,5-dimethyl-2-(pyridin-3-yl)-thiazolidine-4-carboxylic acid can be obtained in the following manner:

Nicotinaldehyde (34 g) is added in the course of 5 minutes, at a temperature of the order of 73° C., to a solution of D,L-penicillamine (30 g) in a mixture of ethanol (860 cc) and distilled water (320 cc), heated to the boil, and heating is continued at this temperature for 2 hours 15 minutes, with stirring. After cooling to a temperature of the order of 20° C. and stirring for 16 hours, the solvent is evaporated off under reduced pressure (20 mm Hg; 2.7 kPa) at a temperature of the order of 50° C. The residue is taken up in ethanol (250 cc) and the solvent is evaporated off under reduced pressure (20 mm Hg; 2.7 kPa) at a temperature of the order of 50° C. This operation is repeated once and the residue finally collected is then dissolved in boiling ethanol (250 cc). The solution obtained is cooled at a temperature of the order of 4° C. for 16 hours. The crystals which have appeared are filtered off, washed 3 times with ethanol cooled to a temperature of the order of 4° C. (30 cc in total) and then 3 times with diethyl ether (45 cc in total) and dried under reduced pressure (20 mm Hg; 2.7 kPa) at a temperature of the order of 20° C., in the presence of potassium hydroxide pellets. This gives a product (26.7 g) melting at 163° C.

The mother liquors from crystallisation are concentrated to dryness under reduced pressure (20 mm Hg; 2.7 kPa) at a temperature of the order of 50° C. This gives a thick oil (27 g). This oil is dissolved in boiling acetonitrile (80 cc). After cooling at a temperature of the order of 4° C. for 1 hour, the crystals which have appeared are filtered off, washed 3 times with acetonitrile cooled to a temperature of the order of 4° C. (30 cc in total) and dried under reduced pressure (20 mm Hg; 2.7 kPa) at a temperature of the order of 20° C., in the presence of potassium hydroxide pellets. This gives a product melting at 160° C. (12.4 g). This product is combined with the batch from the first crystallisation and is dissolved in boiling ethanol (150 cc). Decolourising charcoal (0.5 g) is added to the solution obtained and the mixture is filtered hot. The filtrate is cooled at a temperature of the order 4° C. for 1 hour. The crystals which have appeared are filtered off, washed 3 times with ethanol cooled to a temperature of the order of 4° C. (30 cc in total) and dried under reduced pressure (20 mm Hg; 2.7 kPa) at a temperature of the order of 20° C., in the presence of potassium hydroxide pellets. This gives 5,5-dimethyl-2-(pyridin-3-yl)-thiazolidine-4-carboxylic acid (22.8 g) in the form of white crystals melting at 173° C.

EXAMPLE 9

A solution of 3-(pyridin-3-yl)-1H,3H-pyrrolo[1,2-c]thiazole-7-carboxylic acid (11.1 g) and N,N'-carbonyldiimidazole (10.9 g) in anhydrous tetrahydrofuran (150 cc) is stirred under dry nitrogen at a temperature of the order of 20° C. for 2 hours. A solution of butylamine amine (7.3 g) in anhydrous tetrahydrofuran (20 cc) is added to the solution obtained in the course of 1 hour, at a temperature of between 23° C. and 27° C. The suspension obtained is stirred for 72 hours at a temperature of the order of 25° C. and then treated with distilled water (35 cc). The solvent is evaporated off under reduced pressure (20 mm Hg; 2.7 kPa) at a temperature of the order of 50° C. The solid obtained is suspended in distilled water (150 cc) and the crystals are filtered off, washed 5 times with distilled water (150 cc in total) and dried under reduced pressure (20 mm Hg; 2.7 kPa) at a temperature of the order of 20° C., in the presence of potassium hydroxide pellets. This gives a moist product (14.8 g) melting at 159° C. This product is dissolved in boiling ethanol (65 cc). The solution obtained is treated with decolourising charcoal (0.5 g) and filtered hot. The filtrate is cooled at a temperature of the order of 4° C. for 16 hours. The crystals which have appeared are filtered off, washed 3 times with ethanol cooled to a temperature of the order of 4° C. (20 cc in total) and dried under reduced pressure (20 mm Hg; 2.7 kPa) at a temperature of the order of 20° C., in the presence of potassium hydroxide pellets. This gives N-butyl-3-(pyridin-3-yl)-1H,3H-pyrrolo[1,2-c]thiazole-7-carboxamide (9.5 g) in the form of white crystals melting at 165° C.

The 3-(pyridin-3-yl)-1H,3H-pyrrolo[1,2-c]thiazole-7-carboxylic acid is prepared as in Example 2.

EXAMPLE 10

A solution of 3-(pyridin-3-yl)-1H,3H-pyrrolo[1,2-c]thiazole-7-carboxylic acid (9.1 g) and N,N'-carbonyldimidazole (8.9 g) in anhydrous tetrahydrofuran (40 cc) is stirred under dry nitrogen at a temperature of the order of 25° C. for 1 hour 45 minutes. A solution of 3 N,N-diethylaminopropylamine (9.6 g) in anhydrous tetrahydrofuran (15 cc) is added to the solution obtained in the course of 20 minutes, at a temperature of between 25° C. and 29° C. The solution obtained is stirred at a temperature of the order of 25° C. for a further 2 hours 20 minutes and distilled water (30 cc) is then added to the reaction mixture. The solvent is evaporated off under reduced pressure (20 mm Hg; 2.7 kPa) at a temperature of the order of 50° C. and the residue is taken in distilled water (500 cc). A product crystallises; the suspension is kept at a temperture of the order of 4° C. for 16 hours. The crystals are filtered off, washed 10 times with distilled water (800 cc in total) and dried under reduced pressure (20 mm Hg; 2.7 kPa) at a temperature of the order of 20° C., in the presence of potassium hydroxide pellets. This gives a product (11 g). This product is combined with the product prepared in the same way in another earlier operation (3 g) and is dissolved in a boiling mixture of ethyl acetate and cyclohexane (50/50 by volume) (80 cc). The solution obtained is treated with decolourising charcoal (0.5 g) and filtered hot. The filtrate is cooled at a temperature of the order of 4° C. for 1 hour 30 minutes. The crystals which have appeared are filtered off, washed twice with a mixture of ethyl acetate and cyclohexane (50/50 by volume) cooled to a temperature of the order of 4° C. (10 cc in total) and dried under reduced pressure (20 mm Hg; 2.7 kPa) at a temperature of the order of 20° C., in the presence of potassium hydroxide pellets. This gives N-(3-diethylaminopropyl)-3-(pyridin-3-yl)-1H,3H-pyrrolo[1,2-c]thiazole-7-carboxamide (10.9 g) in the form of white crystals melting at 119° C.

The 3-(pyridin-3-yl)-1H,3H-pyrrolo[1,2-c]thiazole-7-carboxylic acid is prepared as in Example 2.

EXAMPLE 11

A 2 N aqueous solution of sodium hydroxide (13 cc) is added in the course of 5 minutes, at a temperature of between 20° and 30° C., to a solution of ethyl 6-{[3-(pyridin-3-yl)-1H,3H-pyrrolo[1,2-c]thiazol-7-yl]carbonylamino}-hexanoate (5 g) in ethanol (60 cc). The solution is stirred at a temperature of the order 20° C. for 16 hours and is then concentrated to dryness under reduced pressure (20 mm Hg; 2.7 kPa) at a temperature of the order of 40° C. The residue obtained is dissolved in distilled water (50 cc) and the solution obtained is extracted twice with ethyl acetate (40 cc in total), treated with decolourising charcoal (0.5 g) and filtered, and the filtrate is brought to a pH of the order of 4 by adding a 0.5 N aqueous solution of hydrochloric acid. The crystals which have appeared are filtered off, washed 5 times with distilled water (100 cc in total) and dried under reduced pressure (20 mm Hg; 2.7 kPa) at a temperature of the order of 20° C., in the presence of potassium hydroxide pellets. This gives a crude product (4.1 g) melting at 148° C. This product is dissolved in boiling ethanol (65 cc). The solution obtained is treated with decolourising charcoal (0.5 g) and filtered hot. The filtrate is cooled at a temoerature of the order of 4° C. for 1 hour. The crystals which have appeared are filtered off, washed twice with ethanol cooled to a temperature of the order of 4° C. (6 cc in total) and 3 times with diethyl ether (15 cc in total) and then dried under reduced pressure (20 mm Hg; 2.7 kPa) at a temperature of the order of 20° C., in the presence of potassium hydroxide pellets. This gives 6-{[3-(pyridin-3-yl)-1H,3H-pyrrolo[1,2-c]thiazol-7-yl]-carbonylamino}-hexanoic acid (3.4 g) in the form of white crystals melting at 165° C.

The ethyl 6-{[3-(pyridin-3-yl)-1H,3H-pyrrolo[1,2-c]thiazol-7-yl]-carbonylamino}-hexanoate is prepared in the following manner:

A solution of ethyl 6-aminohexanoate (3.9 g) and triethylamine (4.95 g) in 1,2-dichloroethane (100 cc) is added in the course of 25 minutes, at a temperature of between 21° C. and 33° C., to a suspension of 7-chloroformyl-3-(pyridin-3-yl)-1H,3H-pyrrolo[1,2-c]thiazole hydrochloride (6.15 g) in 1,2-dichloroethane (50 cc). The solution obtained is stirred at a temperature of the order of 20° C. for 16 hours and is then diluted with methylene chlorid (100 cc), washed once with an N aqueous solution of sodium hydroxide (60 cc) and 5 times with distilled water (500 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order 50° C. This gives a crude product (7.8 g). This product is chromatographed on a column of diameter 6 cm, containing silica (0.04-0.063 mm) (480 g). Elution is carried out with mixtures of ethyl acetate and methanol under a pressure of 0.5 bar (51 kPa), 100 cc fractions being collected. The first 18 fractions from elution with pure ethyl acetate and the next 5 fractions from elution with a mixture of ethyl acetate and methanol (90/10 by volume) are discarded and the next 15 fractions from elution with a mixture of ethyl acetate and methanol (90/10 by volume) are combined and concentrated to dryness under reduced pressure (20 mm Hg; 2.7 kPa) at a temperature of the order of 50° C. This gives ethyl 6-{[3-(pyridin-3-yl)-1H,3H-pyrrolo[1,2-c]thiazol-7-yl]-carbonylamino}-hexanoate (5 g) in the form of cream crystals melting at 126° C.

The 7-chloroformyl-3-(pyridin-3-yl)-1H,3H-pyrrolo[1,2-c]thiazole hydrochloride is prepared in the following manner:

A suspension of 3-(pyridin-3-yl)-1H,3H-pyrrolo[1,2-c]thiazole-7-carboxylic acid (9.8 g) in a mixture of thionyl chloride (23.8 g), dimethylformamide (0.1 cc) and 1,2-dichloroethane (100 cc) is heated at the boil for 1 hour 15 minutes. After the reaction mixture has cooled, the solvent is evaporated off under reduced pressure (20 mm Hg; 2.7 kPa) at a temperature of the order of 50° C. The residue obtained is suspended in anhydrous cyclohexane (100 cc) and the crystals are filtered off, washed twice with anhydrous cyclohexane (10 cc in total) and dried under reduced pressure (20 mm Hg; 2.7 kPa) at a temperature of the order of 20° C. This gives 7-chloroformyl-3-(pyridin-3-yl)-1H,3H-pyrrolo[1,2-c]thiazole-7-hydrochloride (12.1 g) in the form of ochre crystals melting at 185° C.

The 3-(pyridin-3-yl)-1H,3H-pyrrolo[1,2-c]thiazole-7-carboxylic acid is prepared as in Example 2.

The ethyl 6-aminohexanoate can be prepared according to C. S. Marvel, J. R. Elliott, F. E. Boettner and H. Yuska, J. Amer. Chem. Soc., 68, 1681 (1946).

EXAMPLE 12

A solution of 3-(pyridin-3-yl)-1H,3H-pyrrolo[1,2-c]thiazole-7-carboxylic acid (11.3 g) and N,N'-carbonyldiimidazole (11.2 g) in anhydrous tetrahydrofuran (150 cc) is stirred under dry nitrogen at a temperature of the order of 20° C. for 1 hour 20 minutes. A solution of 1-(2-aminoethyl)-4-(pyridin-2-yl)-piperazine (15,6 g) in anhydrous tetrahydrofuran (30 cc) is added to the solution obtained in the course of 15 minutes, at a temperature of between 25° C. and 29° C. The solution obtained is stirred at a temperature of the order of 25° C. for 4 hours 30 minutes and distilled water (30 cc) is then added. The solvent is evaporated off under reduced pressure (20 mm Hg; 2.7 kPa) at a temperature of the order of 50° C. and the residue is dissolved in ethyl acetate (500 cc). The solution obtained is washed 6 times with distilled water (600 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. The residue obtained is dissolved in boiling acetonitrile (50 cc). The solution obtained is treated with decolourising charcoal (0.5 g) and filtered hot. The filtrate is cooled at a temperature of the order of 4° C. for 1 hour. The crystals which have appeared are filtered off, washed 4 times with acetonitrile cooled to a temperature of the order of 4° C. (40 cc in total) and dried under reduced pressure (20 mm Hg; 2.7 kPa) at a temperature of the order of 20° C., in the presence of potassium hydroxide pellets. This gives a product (17.8 g) melting at 140° C. This product is chromatographed on a column of diameter 6 cm, containing silica (0.040-0.063 mm) (480 g), elution being carried out with a mixture of ethyl acetate and methanol (80/20 by volume) under a pressure of 0.5 bar (51 kPa) and 100 cc fractions being collected. The first 11 fractions are discarded and the next 21 are combined and concentrated to dryness under reduced pressure (20 mm Hg; 2.7 kPa) at a temperature of the order of 50° C. This gives a product (16 g). This product is dissolved in boiling isopropanol (40 cc). The solution obtained is filtered hot and the filtrate is cooled at a temperature of the order of 4° C. for 1 hour. The crystals which have appeared are filtered off, washed 3 times with isopropanol cooled to a temperature of the order of 4° C. (10 cc in total) and dried under reduced pressure (20 mm Hg; 2.7 kPa) at a temperature of the order of 20° C., in the presence of potassium hydroxide pellets. This gives N-{2-[4-(pyridin-2-yl)-piperazin-1-yl]-ethyl}3-(pyridin-3-yl)-1H,3H-pyrrolo[1,2-c]thiazole-7-carboxamide (14.7 g) in the form of white crystals melting at 141° C.

The 3-(pyridin-3-yl)-1H,3H-pyrrolo[1,2-c]thiazole-7-carboxylic acid is prepared as in Example 2. The 1-(2-aminoethyl)-4-(pyridin-2-yl)-piperazine can be prepared according to R. P. Mull et al., J. Med. Pharm. Chem., 5, 944 (1962).

EXAMPLE 13

A solution of 3-(pyridin-3-yl)-1H,3H-pyrrolo[1,2-c]thiazole-7-carboxylic acid (7.4 g) and N,N'-carbonyldiimidazole (7.3 g) in anhydrous tetrahydrofuran (120 cc) is stirred under dry nitrogen at a temperature of the order of 20° C. for 1 hour 15 minutes. A solution of benzylamine (7.2 g) in anhydrous tetrahydrofuran (20 cc) is added to the solution obtained in the course of 10 minutes, at a temperature of the order of 10° C. After stirring for 10 minutes at a temperature of the order of 20° C., precipitation is observed. After stirring for 16 hours at a temperature of the order of 20° C., distilled water (30 cc) is added to the reaction mixture and the solvent is evaporated off under reduced pressure (20 mm Hg; 2.7 kPa) at a temperature of the order of 40° C. The residue obtained is suspended in distilled water (250 cc). The crystals which have appeared are filtered off, washed twice with ethanol (20 cc in total) and 3 times with diethyl ether (45 cc in total) and then dried under reduced pressure (20 mm Hg; 2.7 kPa) at a temperature of the order of 20° C., in the presence of potassium hydroxide pellets. This gives a crude product (10.5 g). This product is dissolved in boiling ethanol (480 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol cooled to a temperature of the order of 4° C. (20 cc in total) and 3 times with diethyl ether (30 cc in total) and then dried under reduced pressure (20 mm Hg; 2.7 kPa) at a temperature of the order of 20° C., in the presence of potassium hydroxide pellets. This gives N-benzyl-3-(pyridin-3-yl)-1H,3H-pyrrolo[1,2-c]-thiazole-7-carboxamide (8.2 g) in the form of white crys-tals melting at 200° C.

The 3-(pyridin-3-yl)-1H,3H-pyrrolo[1,2-c]thiazole7-carboxylic acid is prepared as in Example 2.

EXAMPLE 14

A solution of 3-(pyridin-3-yl)-1H,3H-pyrrolo[1,2-c]thiazole-7-carboxylic acid (4.9 g) and N,N'-carbonyldiimidazole (4.9 g) in anhydrous tetrahydrofuran (80 cc) is stirred under dry nitrogen at a temperature of the order 20° C. for 3 hours. A solution of histamine. (5 g) in dimethylformamide (60 cc) is added to the solution obtained in the course of 5 minutes, at a temperature of the order of 15° C. The solution obtained is stirred at a temperature of the order of 20° C. for 20 hours. Distilled water (30 cc) is then added to the reaction mixture and the solvent is evaporated off under reduced pressure (5 mm Hg; 0.7 kPa) at a temperature of the order of 50° C. The oily residue obtained is taken up in distilled water (350 cc). A product crystallises. The suspension obtained is stirred at a temperature of the order of 4° C. for 1 hour. The crystals which have appeared are filtered off, washed 3 times with distilled water cooled to a temperature of the order of 4° C. (30 cc in total) and dried under reduced pressure (20 mm Hg; 2.7 kPa) at a temperature of the order of 20° C., in the presence of potassium hydroxide pellets. This gives a product (6.6 g) melting at 198° C. This product is combined with the product prepared in the same way in another earlier operation (5.3 g) and dissolved in a boiling mixture of ethanol and distilled water (50/50 by volume) (100 cc). The solution obtained is treated with decolourising charcoal (0.5 g) and filtered hot. The filtrate is cooled at a temperature of the order of 4° C. for 1 hour. The crystals which have appeared are filtered off, washed twice with a mixture of ethanol and distilled (50/50 by volume) (20 cc in total), twice with ethanol (20 cc in total) and twice with diethyl ether (40 cc in total) and then dried under reduced pressure (20 mm Hg; 2.7 kPa) at a temperature of the order of 20° C., in the presence of potassium hydroxide pellets. This gives N-[2-(imidazol-4-yl)-ethyl]-3-(pyridin-3-yl)-1H,3H-pyrrolo[1,2-c]thiazole-7-carboxamide (10.6 g) in the form of cream crystals melting at 201° C.

The 3-(pyridin-3-yl)-1H,3H-pyrrolo[1,2-c]thiazole-7-carboxylic acid is prepared as in Example 2.

EXAMPLE 15

7-Chloroformyl-3-(pyridin-3-yl)-1H,3H-pyrrolo[1,2-c]thiazole hydrochloride (12.1 g) is added in the course of 1 hour, at a temperature of between 25° C. and 34° C., to a solution of aniline (11.3 g) and triethylamine (16.2 g) in 1,2-dichloroethane (300 cc). The suspension obtained is stirred at a temperature of the order of 20° C. for 16 hours. The reaction mixture is then washed 3 times with a 2 N aqueous solution of sodium hydroxide (300 cc in total) and 7 times with distilled water (1400 cc in total). The organic phase is extracted 3 times with a 5 N aqueous solution of hydrochloric acid (300 cc in total) and the aqueous extracts are combined, washed 3 times with methylene chloride (150 cc in total), treated with decolourising charcoal (0.5 g) and filtered. The filtrate is brought to a pH of the order of 10 by adding a 10 N aqueous solution of sodium hydroxide and extracted 3 times with methylene chloride (450 cc in total). The organic extracts are combined, washed 3 times with distilled water (600 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives an oily product (16.2 g). This product is dissolved in a boiling mixture of ethyl acetate and cyclohexane (50/50 by volume) (60 cc). The solution obtained is cooled at a temperature of the order of 4° C. for 30 minutes. The crystals which have appeared are filtered off, washed 3 times with a mixture of ethyl acetate and cyclohexane (50/50 by volume) (20 cc in total) and dried under reduced pressure (20 mm Hg; 2.7 kPa) at a temperature of the order of 20° C., in the presence of potassium hydroxide pellets. This gives a product (5.8 g) melting at 133° C. This product is combined with the product prepared in the same manner in another earlier operation (0.6 g) and is dissolved in a boiling mixture of ethyl acetate and cyclohexane (50/50 by volume) (110 cc). The solution obtained is treated with decolourising charcoal (0.5 g) and filtered hot. The filtrate is cooled at a temperature of the order of 4° C. for 1 hour. The crystals which have appeared are filtered off, washed twice with a mixture of ethyl acetate and cyclohexane (5C/50 by volume) cooled to a temperature of the order of 4° C. (10 cc) and dried under reduced pressure (20 mm Hg; 2.7 kPa) at a temperature of the order of 20° C., in the presence of potassium hydroxide pellets. This gives N-phenyl-3-(pyridin-3-yl)-1H,3H-pyrrolo[1,2-c]thiazole-7-carboxamide (5.3 g) in the form of white crystals melting at 135° C.

The 7-chloroformyl-3-(pyridin-3-yl)-1H,3H-pyrrolo[1,2-c]thiazole hydrochloride is prepared as in Example 11.

EXAMPLE 16

7-Chloroformyl-3-(pyridin-3-yl)-1H,3H-pyrrolo[1,2-c]thiazole hydrochloride (6 g) is added in small portions at a time, in the course of 15 minutes, at a temperature of the order 20° C., to a solution of 4-chloroaniline (5.1 g) and triethylamine (8.1 g) in 1,2-dichloroethane (150 cc). The solution is stirred at a temperature of the order of 20° C. for 16 hours and is then diluted with methylene chloride (100 cc), washed twice with distilled water (100 cc in total), twice with a 2 N aqueous solution of sodium hydroxide (100 cc in total) and 5 times with distilled water (500 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude solid (9 g). This product is dissolved in boiling acetonitrile (150 cc) and the solution obtained is treated with decolourising charcoal (0.5 g) and filtered hot. The filtrate is cooled at a temperature of the order of 4° C. for 16 hours. The crystals which have appeared are filtered off, washed twice with acetonitrile cooled to a temperature of the order of 4° C. (15 cc in total) and dried under reduced pressure (20 mm Hg; 2.7 kPa) at a temperature of the order of 20° C. in the presence of potassium hydroxide pellets. This gives N-(4-chlorophenyl)-3-(pyridin-3-yl)-1H,3H-pyrrolo[1,2-c]thiazole-7-carboxamide (4.3 g) in the form of cream crystals melting at 187° C.

The 7-chloroformyl-3-(pyridin-3-yl)-1H,3H-pyrrolo[1,2-c]thiazole hydrochloride is prepared as in Example 11.

EXAMPLE 17

A solution of 3-(pyridin-3-yl)-1H,3H-pyrrolo[1,2-c]thiazole-7carboxylic acid (2 g) and N,N'-carbonyldiimidazole (1.45 g) in anhydrous tetrahydrofuran (40 cc) is stirred at a temperature of the order of 20° C. for 4 hours. The solution obtained is treated with decolourising charcoal (0.5 g) and filtered, and the filtrate is concentrated to dryness under reduced pressure (20 mm Hg; 2.7 kPa) at a temperature of the order of 45° C. The residue is taken up in distilled water (100 cc) and the suspension obtained is stirred at a temperature of the order of 20° C. for 30 minutes. The crystals are filtered off, washed 3 times with distilled water (60 cc in total) and dried under reduced pressure (20 mm Hg; 2.7 kPa) at a temperature of the order of 20° C., in the presence of potassium hydroxide pellets. This gives a crude product (2 g). This product is dissolved in boiling isopropanol (35 cc). The solution obtained is cooled at a temperature of the order of 4° C. for 1 hour. The crystals which have appeared are filtered off, washed twice with isopropanol cooled to a temperature of the order of 4° C. (20 cc in total) and twice with isopropyl ether (20 cc in total) and then dried under reduced pressure (20 mm Hg; 2.7 kPa) at a temperature of the order of 20° C., in the presence of potassium hydroxide pellets. This gives 7-(imidazol-1-yl-carbonyl)-3-(pyridin-3-yl)-1H,3H-pyrrolo[1,2-c]thiazole (1.7 g) in the form of cream crystals melting at 117° C.

The 3-(pyridin-3-yl)-1H,3H-pyrrolo[1,2-c]thiazole-7-carboxylic acid is prepared as in Example 2.

EXAMPLE 18

A solution of 7-(imidazol-1-yl-carbonyl)-3-(pyridin-3-yl)-1H,3H-pyrrolo[1,2-c]thiazole (16 g) and 2-aminopyridine (10.2 g) in anhydrous dimethylformamide (150 cc) is heated for 5 hours 30 minutes at a temperature of the order of 150° C. The solution is then concentrated to dryness under reduced pressure (20 mm Hg; 2.7 kPa) at a temperature of the order of 80° C. and the residual oil is taken up in distilled water (500 cc). Crystals appear. The suspension is stirred at a temperature of the order of 20° C. for 16 hours. The crystals are filtered off, washed 3 times with distilled water (300 cc in total) and dried under reduced pressure (20 mm Hg; 2.7 kPa) at a temperature of the order of 20° C., in the presence of potassium hydroxide pellets. This gives a crude product (14.6 g) melting at 141° C. This product is dissolved in boiling ethanol (75 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol cooled to a temperature of the order of 4° C. (10 cc in total) and 3 times with diethyl ether (15 cc in total) and then dried under reduced pressure (20 mm Hg; 2.7 kPa) at a temperature of the order of 20° C., in the presence of potassium hydroxide pellets. This gives N-(pyridin-2-yl)-3-(pyridin-3-yl)-1H,3H-pyrrolo[1,2-c]thiazole-7-carboxamide (11.6 g) in the form of beige crystals melting at 145° C.

The 7-(imidazol-1-yl-carbonyl)-3-(pyridin-3-yl)-1H,3H-pyrrolo[1,2-c]thiazole is prepared as in Example 17.

EXAMPLE 19

7-Chloroformyl-3-(pyridin-3-yl)-1H,3H-pyrrolo-[1,2-c]thiazole hydrochloride (6 g) is added in small portions at a time, in the course of 20 minutes, at a temperature of between 19° C. and 26° C., to a solution of 3-aminopyridine (3.8 g) and triethylamine (8.1 g) in 1,2-dichloroethane (150 cc). The suspension obtained is stirred at a temperature of the order of 20° C. for 16 hours. The crystals are filtered off, washed 3 times with 1,2-dichloroethane (75 cc in total), 3 times with isopropyl ether (75 cc in total) and then 5 times with distilled water (150 cc in total) and dried in air. This gives a crude product (6 g) melting at 210° C. This product is taken up in boiling ethanol (75 cc). The turbid solution obtained is treated with decolourising charcoal (0.5 g) and filtered hot. The filtrate is cooled at a temperature of the order of 4° C. for 16 hours. The crystals which have appeared are filtered off, washed 3 times with ethanol (15 cc in total) and then 3 times with diethyl ether (45 cc in total) and dried under reduced pressure (20 mm Hg; 2.7 kPa) at a temperature of the order of 20° C., in the presence of potassium hydroxide pellets. This gives N-pyridin-3-yl-3-(pyridin-3-yl)-1H,3H-pyrrolo-[1,2-c]thiazole-7-carboxamide (2.5 g) in the form of white crystals melting at 220° C.

The 7-chloroformyl-3-(pyridin-3-yl)-1H,3H-pyrrolo-[1,2-c]thiazole hydrochloride is prepared as in Example 11.

EXAMPLE 20

A solution of 3-(pyridin-3-yl)-1H,3H-pyrrolo-1,2-c]thiazole-7-carboxylic acid (10 g) and N,N'-carbonyldimidazole (9.9 g) in anhydrous tetrahydrofuran (160 cc) is stirred under dry nitrogen at a temperature of the order of 20° C. for 1 hour 15 minutes. Hydrazine hydrate (6.1 g) is added to the solution obtained in the course of 10 minutes, at a temperature of the order of 15° C. After stirring for 1 hour at a temperature of the order of 20° C., distilled water (100 cc) is added to the reaction mixture and the solvent is evaporated off under reduced pressure (20 mm Hg; 2.7 kPa) at a temperature of the order of 55° C. The solid obtained is suspended in distilled water (400 cc). After stirring for 15 minutes at a temperature of the order of 4° C., the crystals which have appeared are filtered off, washed 3 times with distilled water (150 cc in total), 3 times with ethanol cooled to a temperature of the order of 4° C. (30 cc in total) and 3 times with diethyl ether (45 cc in total) and then dried under reduced pressure (20 mm Hg; 2.7 kPa) at a temperature of the order of 20° C., in the presence of potassium hydroxide pellets. This gives a crude product (9 g) melting at 185° C. This product, combined with the product prepared in the same manner in another earlier operation (3.9 g), is dissolved in boiling ethanol (350 cc). The solution obtained is treated with decolourising charcoal (0.5 g) and filtered hot. The filtrate is cooled at a temperature of the order of 4° C. for 1 hour. The crystals which have appeared are filtered off, washed 3 times with ethanol cooled to a temperature of the order 4° C. (30 cc in total) and 3 times with diethyl ether (30 cc in total) and then dried under reduced pressure (20 mm Hg; 2.7 kPa) at a temperature of the order of 20° C., in the presence of potassium hydroxide pellets. This gives a product (11.2 g) melting at 186° C. This product is dissolved in boiling ethanol (300 cc). The solution obtained is cooled at a temperature of the order of 4° C. for 30 minutes. The crystals which have appeared are filtered off, washed 3 times with ethanol cooled to a temperature of the order of 4° C. (15 cc in total) and 3 times with diethyl ether (15 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carbohydrazide (10.4 g) in the form of cream crystals melting at 187° C.

The 3-(pyridin-3-yl)-1H,3H-pyrrolo[1,2-c]thiazole-7-carboxylic acid is prepared as in Example 2.

EXAMPLE 21

A solution of 3-(pyridin-3-yl)-1H,3H-pyrrolo-[1,2-c]thiazole-7-carboxylic acid (5 g) and N,N'-carbonyldiimidazole (4.95 g) in anhydrous tetrahydrofuran (50 cc) is stirred at a temperature of the order of 20° C. for 1 hour. A solution of 1-(2-hydroxyethyl)-piperazine (4.7 g) in tetrahydrofuran (50 cc) is then added in the course of 20 minutes at a temperature of the order of 25° C. The solution is stirred at a temperature of the order of 20° C. for 16 hours and is then treated with distilled water (40 cc). The solvent is evaporated off under reduced pressure (20 mm Hg; 2.7 kPa) at a temperature of the order of 45° C. The residue obtained is dissolved in methylene chloride (350 cc). The solution obtained is washed twice with distilled water (200 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (7.2 g). This product is chromatographed on a column of diameter 6 cm, containing silica (0.04–0.063 mm) (480 g). Elution is carried out with a mixture (9/1 by volume) of acetonitrile and aqueous ammonia (d=0.92) under a pressure of 0.5 bar (51 kPa), 100 cc fractions being collected. The first 15 fractions are discarded; the next fraction is concentrated to dryness under reduced pressure (20 mm Hg; 2.7 kPa) at a temperature of the order of 60° C. This gives a product (1.4 g). This product is dissolved in ethanol (20 cc) and the solution obtained is added in the course of 35 minutes to a 5 N ethanolic solution of hydrogen chloride (20 cc). The suspension obtained is left to stand at a temperature of the order of 20° C. for 3 days. The crystals are filtered off, washed twice with ethanol (10 cc in total) and twice with diethyl ether (20 cc in total) and then dried under reduced pressure (20 mm Hg; 2.7 kPa) at a temperature of the order of 20° C., in the presence of potassium hydroxide pellets. This gives 7-[4-(2-hydroxyethyl)-piperazin-1-yl]-carbonyl-3-(pyridin-3-yl)-1H,3H-pyrrolo[1,2-c]thiazole as the trihydrochloride monohydrate (1.5 g) in the form of white crystals melting at 194° C.

The 3-(pyridin-3-yl)-1H,3H-pyrrolo[1,2-c]thiazole-7-carboxylic acid is prepared as in Example 2.

EXAMPLE 22

A solution of 3-(pyridin-3-yl)-1H,3H-pyrrolo-[1,2-c]thiazole-7-carboxylic acid (4.9 g) and N,N'-carbonyldiimidazole (4.9 g) in anhydrous tetrahydrofuran (80 cc) is stirred under dry nitrogen at a temperature of the order of 20° C. for 1 hour 30 minutes. A solution of 1-benzylpiperazine (5.3 g) in anhydrous tetrahydrofuran (20 cc) is then added to the solution obtained in the course of 5 minutes, at a temperature of between 24 and 27° C. The solution is stirred at a temperature of the order of 20° C. for 16 hours and is then filtered, the filtrate is concentrated to dryness under reduced pressure (20 mm Hg; 2.7 kPa) at a temperature of the order of 40° C. This gives a crude product (13.9 g), which is chromatographed on a column of diameter 6 cm, containing silica (0.04–0.063 mm) (480 g). Elution is carried out with a mixture of methylene chloride and methanol (9/1 by volume) under a pressure of 0.5 bar (51 kPa), 100 cc fractions being collected. The first 8 fractions are discarded and the next 9 fractions are combined and concentrated to dryness under reduced pressure (20 mm Hg; 2.7 kPa) at a temperature of the order of 40° C. This gives a product (9 g). This product is dissolved in acetone (90 cc). The solution obtained is treated with decolourising charcoal (0.5 g) and filtered. A solution of oxalic acid (5.9 g) in acetone (60 cc) is then added to the solution. The suspension obtained is stirred at a temperature of the order of 20° C. for 30 minutes and the crystals are filtered off, washed 5 times with acetone (100 cc in total) and dried under reduced pressure (20 mm Hg; 2.7 kPa) at a temperature of the order of 20° C., in the presence of potassium hydroxide pellets. This gives a product (12.6 g), which is dissolved in distilled water (250cc). The solution obtained is brought to a pH of the order of 12 by adding a 10 N aqueous solution of sodium hydroxide (10 cc) and is extracted 3 times with ethyl acetate (300 cc in total). The organic extracts are combined, washed twice with distilled water (160 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a product (8 g). This product is dissolved in a boiling mixture of cyclohexane and ethyl acetate (80/20 by volume) (50 cc). The solution obtained is treated with decolourising charcoal (0.5 g) and filtered hot. The filtrate is cooled at a temperature of the order of 20° C. for 3 hours. The crystals which have appeared are filtered off, washed twice with a mixture of cyclohexane and ethyl acetate (80/20 by volume) (20 cc in total) and once with diethyl ether (15 cc) and then dried under reduced pressure (20 mm Hg; 2.7 kPa) at a temperature of the order of 20° C., in the presence of potassium hydroxide pellets. This gives 7-(4-benzylpiperazin-1-yl)-carbonyl-3-(pyridin-3-yl)-1H,3H-pyrrolo[1,2-c]thiazole (3.6 g) in the form of white crystals melting at 95° C.

The 3-(pyridin-3-yl)-1H,3H-pyrrolo[1,2-c]thiazole-7-carboxylic acid is prepared as in Example 2.

EXAMPLE 23

A solution of 3-(pyridin-3-yl)-1H,3H-pyrrolo[1,2-c]thiazole-7-carboxylic acid (7.4 g) and N,N'-carbonyldiimidazole (7.3 g) in anhydrous tetrahydrofuran (120 cc) is stirred under dry nitrogen at a temperature of the order of 20° C. for two hours. A solution of N-phenylpiperazine (15.3 g) in anhydrous tetrahydrofuran (40 cc) is added to the solution in the course of 15 minutes, at a temperature of the order of 10° C., and stirring is continued for three hours at a temperature of the order of 20° C. Distilled water (30 cc) is then added to the reaction mixture and the solvent is evaporated off under reduced pressure (20 mm Hg; 2.7 kPa) at a temperature of the order of 50° C. The crude oil obtained is dissolved in boiling acetonitrile (100 cc); the solution is treated with decolourising charcoal (0.5 g) and filtered hot. The filtrate is cooled at a temperature of the order of 4° C. for 1 hour. The crystals which have appeared are filtered off, washed 3 times with acetonitrile cooled to a temperature of the order of 4° C. (25 cc in total) and 3 times with diethyl ether (45 cc in total) and then dried under reduced pressure (20 mm Hg; 2.7 kPa) at a temperature of the order of 20° C., in the presence of potassium hydroxide pellets. This gives a product (8.1 g) melting at 144° C. This product, combined with the product prepared in the same manner in another earlier operation (5.5 g), is dissolved in boiling ethanol (100 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol cooled to a temperature of the order of 4° C. (20 cc in total) and twice with diethyl ether (30 cc in total) and dried under reduced pressure (20 mm Hg; 2.7 kPa) at a temperature of the order of 20° C., in the presence of potassium hydroxide pellets. This gives 7-[(4-phenylpiperazin-1-yl)-carbonyl]-3-(pyridin-3-yl)-1H,3H-pyrrolo[1,2-c]thiazole (11.8 g) in the form of white crystals melting at 146° C.

The 3-(pyridin-3-yl)-1H,3H-pyrrolo[1,2-c]thiazole-7-carboxylic acid is prepared as in Example 2.

EXAMPLE 24

A solution of 3-(pyridin-3-yl)-1H,3H-pyrrolo[1,2-c]thiazole-7-carboxylic acid (4.93 g) and N,N'-carbonyldiimidazole (4.9 g) in anhydrous tetrahydrofuran (80 cc) is stirred under a stream of dry nitrogen for 1 hour 30 minutes. A solution of 1-(pyridin-2-yl)-piperazine (4.9 g) in anhydrous tetrahydrofuran (20 cc) is then added to the solution obtained in the course of 5 minutes, at a temperature of the order of 25° C. The solution obtained is stirred at a temperature of the order of 20° C. for 16 hours and is then diluted with distilled water (90 cc) at a temperature of the order of 10° C. and filtered. The filtrate is treated with distilled water (180 cc) at a temperature of the order of 4° C. The suspension obtained is treated with distilled water (90 cc) and is then stirred at a temperature of the order of 4° C. for 1 hour. The crystals are filtered off, washed 3 times with distilled water (60 cc in total) and dried under reduced pressure (20 mm Hg; 2.7 kPa) at a temperature of the order of 20° C., in the presence of potassium hydroxide pellets. This gives a crude product (7.05 g) melting at 140° C. This product is dissolved in boiling ethanol (28 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol cooled to a temperature of the order of 4° C. (10 cc in total) and once with diethyl ether (10 cc) and then dried under reduced pressure (20 mm Hg; 2.7 kPa) at a temperature of the order of 20° C., in the presence of potassium hydroxide pellets. This gives 7-[4-(pyridin-2-yl)-piperazin-1-yl]-carbonyl-3-(pyridin-3-yl)-1H,3H-pyrrolo[1,2-c]thiazole (5.7 g) in the form of cream crystals melting at 142° C.

The 3-(pyridin-3-yl)-1H,3H-pyrrolo[1,2-c]thiazole-7-carboxylic acid is prepared as in Example 2.

EXAMPLE 25

A solution of 3-(pyridin-3-yl)-1H,3H-pyrrolo[1,2-c]thiazole-7-carboxylic acid (5 g) and N,N'-carbonyldiimidazole (5 g) in anhydrous tetrahydrofuran (50 cc) is stirred under a stream of dry nitrogen for 1 hour at a temperature of the order of 20° C. A solution of 1-(pyrimidin-2-yl)-piperazine (5.7 g) in anhydrous tetrahydrofuran (50 cc) is added to the solution obtained in the course of 15 minutes, at a temperature of the order of 25° C. The solution is then stirred at a temperature of the order of 20° C. for 3 hours. Distilled water (100 cc) is then added to the suspension obtained. The crystals are filtered off, washed 5 times with distilled water (250 cc in total), 5 times with ethanol (25 cc in total) and 5 times with diethyl ether (50 cc in total) and dissolved in boiling ethanol (250 cc). The solution obtained is treated with decolourising charcoal (0.5 g) and filtered hot. The filtrate is cooled at a temperature of the order of 4° C. for 72 hours. The crystals which have appeared are filtered off, washed twice with ethanol cooled to a temperature of the order of 4° C. (30 cc in total) and dried under reduced pressure (20 mm Hg; 2.7 kPa) at a temperature of the order of 20° C., in the presence of potassium hydroxide pellets. This gives 7-[4-(pyrimidin-2-yl)-piperazin-1-yl]-carbonyl-3-(pyridin-3-yl)-1H,3H-pyrrolo[1,2-c]thiazole (5.4 g) in the form of white crystals melting at 209° C.

The 3-(pyridin-3-yl)-1H,3H-pyrrolo[1,2-c]thiazole-7-carboxylic acid is prepared as in Example 2.

EXAMPLE 26

Triethylamine (5.1 g) is added to a solution of the ethoxymagnesium derivative of diethyl malonate in a mixture of ether and ethanol (3/1 by volume) (65 cc), prepared from magnesium (1.34 g) and diethyl malonate (8.8 g); 7-chloroformyl-3-(pyridin-3-yl)-1H,3H-pyrrolo-[1,2-c]thiazole hydrochloride (15 g) is added to the suspension obtained in the course of 15 minutes, at a temperature of between 25° C. and 30° C., and the mixture is then diluted with anhydrous tetrahydrofuran (35 cc) and stirred at a temperature of the order of 20° C. for 16 hours. The reaction mixture is then taken up in a 2 N aqeuous solution of hydrochloric acid (25 cc) and extracted 5 times with ethyl acetate (750 cc in total). The organic extracts are combined, washed 5 times with distilled water (250 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (19 g) melting at 110° C. This product is dissolved in a mixture of acetic acid (25 cc), distilled water (15 cc) and concentrated sulphuric acid (3 cc). The solution obtained is heated at a temperature of the order of 100° C. for 9 hours 30 minutes and is then cooled to a temperature of the order of 20° C., diluted with distilled water (150 cc), treated with decolourising charcoal (0.5 g) and filtered, and the filtrate is brought to a pH of the order of 9 by adding sodium carbonate and extracting 3 times with ethyl acetate (450 cc in total). The organic extracts are combined, washed 3 times with distilled water (450 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 45° C. This gives a product (9.5 g). This product is chromatographed on a column of diameter 6 cm, containing silica (0.04–0.063 mm) (480 g), elution being carried out with mixtures of cyclohexane and ethyl acetate under a pressure of 0.5 bar (51 kPa) and 200 cc fractions being collected. The first 9 fractions from elution with a mixture of ethyl acetate and cyclohexane (80/20 by volume) are discarded. The next 9 fractions from elution with a mixture of ethyl acetate and cyclohexane (85/15 by volume) are combined and concentrated to dryness under reduced pressure (20 mm Hg; 2.7 kPa) at a temperature of the order of 50° C. This gives a product (7.2 g). This product is dissolved in boiling isopropanol (30 cc). The solution obtained is treated with decolourising charcoal (0.5 g) and filtered hot. The filtrate is cooled at a temperature of the order of 4° C. for 1 hour. The crystals which have appeared are filtered off, washed 3 times with isopropanol cooled to a temperature of the order of 4° C. (15 cc in total) and dried under reduced pressure (20 mm Hg; 2.7 kPa) at a temperature of the order of 20° C., in the presence of potassium hydroxide pellets. This gives 7-acetyl-3-(pyridin-3-yl)-1H,3H-pyrrolo[1,2-c]thiazole (5.7 g) in the form of cream crystals melting at 100° C.

The 7-chloroformyl-3-(pyridin-3-yl)-1H,3H-pyrrolo[1,2-c]thiazole hydrochloride is prepared as in Example 11.

The ethoxymagnesium derivative of diethyl malonate is prepared according to G. A. Reynolds and C. R. Hauser, Org. Synth. Coll. Vol 4, 708 (1963).

EXAMPLE 27

A solution of 3-(pyridin-3-yl)-1H,3H-pyrrolo[1,2-c]thiazole-7-carbothioamide (2.6 g) and hydroxylamine hydrochloride (6.95 g) in pyridine (25 cc) is treated with mercuric chloride (2.7 g) and the suspension obtained is stirred at a temperature of the order of 20° C. for 48 hours and is then poured into distilled water (280 cc). The suspension obtained is heated to a temperature of the order of 80° C. and filtered. The filtrate is concentrated to dryness under reduced pressure (20 mm Hg; 2.7 kPa) at a temperature of the order of 70° C. The residue is dissolved in distilled water (100 cc) and the solution obtained is brought to a pH of the order of 10 by adding a 10 N aqueous solution of sodium hydroxide and then extracted 3 times with methylene chloride (300 cc in total). The organic extracts are combined, washed twice with distilled water (100 cc in total), dried over anhydrous magnesium sulphate and filtered, and the filtrate is concentrated to dryness under reduced pressure (20 mm Hg; 2.7 kPa) at a temperature of the order of 50° C. This gives a crude product (2.5 g). This product is chromatographed on a column of diameter 3 cm, containing silica (0.04–0.063 mm) (240 g). Elution is carried out with pure ethyl acetate under a pressure of 0.5 bar (51 kPa), 50 cc fractions being collected. The first 12 fractions are discarded and the next 11 fractions are combined and concentrated to dryness under reduced pressure (20 mm Hg; 2.7 kPa) at a temperature of the order of 50° C. This gives a product (1.6 g). This product is dissolved in ethanol (35 cc) and the solution obtained is treated with a 5.35 N ethanolic solution of hydrogen chloride (2.6 cc) and cooled at a temperature of the order of 4° C. for 16 hours. The crystals which have appeared are filtered off, washed twice with ethanol cooled to a temperature of the order of 4° C. (15 cc in total) and 3 times with diethyl ether (45 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carboxamide-oxime dihydrochloride (1.6 g) in the form of white crystals melting at 206° C.

The 3-(pyridin-3-yl)-1H,3H-pyrrolo[1,2-c]thiazole-7-carbothioamide can be prepared in the following manner:

3-(Pyridin-3-yl)-1H,3H-pyrrolo[1,2-c]thiazole-7-carboxamide (8.1 g) is added to pyridine (100 cc) saturated at a temperature of the order of 20° C. with a gaseous stream of hydrogen sulphide. The suspension obtained is treated with phosphorus pentasulphide (7.3 g) and then heated at the boil for 2 hours under a gaseous stream of hydrogen sulphide. The solution obtained is cooled to a temperature of the order of 20° C. and is then poured into distilled water (1200 cc). The suspension obtained is kept at a temperature of the order of 4° C. for 16 hours. The crystals are filtered off, washed 5 times with distilled water (500 cc in total), 5 times with ethanol (25 cc in total) and 5 times with diethyl ether (100 cc in total) and then dried under reduced pressure (20 mm Hg; 2.7 kPa) at a temperature of the order of 20° C., in the presence of potassium hydroxide pellets. This gives a crude product (7.7 g) melting at 205° C. This product is dissolved in boiling butan-1-ol (180 cc). The solution obtained is cooled at a temperature of the order of 4° C. for 1 hour. The crystals which have appeared are filtered off, washed 3 times with butan-1-ol cooled to a temperature of the order of 4° C. (15 cc in total) and 3 times with diethyl ether (60 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carbothioamide (7.1 g) in the form of cream crystals melting at 205° C.

The 3-(pyridin-3-yl)-1H,3H-pyrrolo[1,2-c]thiazole-7-carboxamide is prepared as in Example 3.

EXAMPLE 28

A suspension of S-methyl 3-(pyridin-3-yl)-1H,3H-pyrrolo[1,2-c]thiazole-7-thiocarboximidate hydroiodide (9.5 g) and N,N-dimethylhydrazine (1.6 g) in ethanol (125 cc) is heated at a temperature of the order of 78° C. for 4 hours 30 minutes. The solution obtained is concentrated to dryness under reduced pressure (20 mm Hg; 2.7 kPa) at a temperature of the order of 60° C. The residue obtained is dissolved in distilled water (250 cc) and the resulting solution is extracted 3 times with ethyl acetate (300 cc in total), treated with decolourising charcoal (0.5 g) and filtered, and the filtrate is brought to a pH of the order of 10 by adding a 10 N aqueous solution of sodium hydroxide and extracted 3 times with ethyl acetate (300 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (4.8 g), which is chromatographed on a column of diameter 4 cm, containing silica (0.04–0.063 mm) (320 g). Elution is carried out under a pressure of 0.5 bar (51 kPa) with mixtures of methylene chloride and methanol, 100 cc fractions being collected. The first 13 fractions from elution with a mixture of methylene chloride and methanol (90/10 by volume) are discarded. The next 4 fractions from elution with a mixture of methylene chloride and methanol (90/10 by volume), the next 9 fractions from elution with a mixture of methylene chloride and methanol (80/20 by volume) and the next 10 fractions from elution with a mixture of methylene chloride and methanol (50/50 by volume) are combined and concentrated to dryness under reduced pressure (20 mm Hg; 2.7 kPa) at a temperature of the order of 60° C. This gives a product (3.1 g), which is dissolved in ethanol (20 cc). The turbid solution obtained is filtered and the filtrate is treated with a 5.35 N ethanolic solution of hydrogen chloride (8.1 cc); the hydrochloride obtained is precipitated from it solution by adding diethyl ether (2 cc). After cooling at a temperature of the the order 4° C. for 16 hours, the crystals are filtered off, washed 5 times with a mixture of diethyl ether and ethanol (50/50 by volume) (75 cc in total) and 5 times with diethyl ether (75 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carboxamide-dimethylhydrazone hydrochloride (2.7 g) in the form of cream crystals melting at 195° C.

The S-methyl 3-(pyridin-3-yl)-1H,3H-pyrrolo[1,2-c]thiazole-7-thiocarboximidate hydroiodide can be prepared in the following manner:

A suspension of 3-(pyridin-3-yl)-1H,3H-pyrrolo[1,2-c]thiazole-7-carbothioamide (7 g) and methyl iodide (4.2 g) in acetone (250 cc) is stirred at a temperature of the order of 20° C. for 16 hours. Dimethylformamide (50 cc) is then added to the suspension and stirring is continued for a further 3 days. The crystals are then filtered off, washed 3 times with acetone (90 cc in total) and dried under reduced pressure (20 mm Hg; 2.7 kPa) at a temperature of the order of 20° C., in the presence of potassium hydroxide pellets. This gives S-methyl 3-(pyridin-3-yl)-1H-3H-pyrrolo[1,2-c]thiazole-7-thiocarboximidate hydroiodide (9.5 g) in the form of yellow crystals melting at 193°–194° C.

The 3-(pyridin-3-yl)-1H,3H-pyrrolo[1,2-c]thiazole-7-carbothioamide is prepared as in Example 27.

EXAMPLE 29

A mixture of 7-chloroformyl-3-(pyridin-3-yl)-1H,3H-pyrrolo[1,2-c]thiazole hydrochloride (3.8 g) and triethylamine (2.55 g) in dioxane (100 cc) is added in the course of 15 minutes to a solution of 3-methoxyaniline (3.1 g) in dioxane (45 cc), heated to the boil. The suspension obtained is heated at a temperature of the order of 100° C. for two hours, with stirring, and the solvent is then evaporated off under reduced pressure (20 mm Hg; 2.7 kPa) at a temperature of the order of 50° C. The residue is taken up in distilled water (150 cc) and extracted 3 times with methylene chloride (300 cc in total). The organic extracts are combined, washed 3 times with distilled water (300 cc in total), 4 times with a 2 N aoueous solution of sodium hydroxide (200 cc in total) and 4 times with distilled water (400 cc in total) and then dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (5.5 g), which is chromatographed on a column of diameter 6 cm, containing silica (0.04–0.063 mm) (480 g). Elution is carried out with mixtures of ethyl acetate and cyclohexane under a pressure 0.5 bar (51 kPa), 200 cc fractions being collected. The first 10 fractions from elution with a mixture of cyclohexane and ethyl acetate (50/5J by volume) and the next 4 fractions from elution with pure ethyl acetate are discarded; the next 12 fractions from elution with pure ethyl acetate are combined and concentrated to dryness under reduced pressure (20 mm Hg; 2.7 kPa) at a temperature of the order of 50° C. This gives a crude product (3 g). This product is dissolved in boiling isopropanol (30 cc). The solution obtained is treated with decolourising charcoal (0.5 g) and filtered hot. The filtrate is cooled at a temperature of the order of 4° C. for 1 hour. The crystals which have appeared are filtered off, washed twice with isopropanol cooled to a temperature of the order of 4° C. (10 cc in total) and twice with isopropyl ether (20 cc in total) and then dried under reduced pressure (20 mm Hg; 2.7 kPa) at a temperature of the order 20° C., in the presence of potassium hydroxide pellets. This gives N-(3-methoxyphenyl)-3-(pyridin-3-yl)-1H,3H-pyrrolo[1,2-c]thiazole-7-carboxamide (1.8 g) in the form of white crystals melting at 85° C.

The 7-chloroformyl-3-(pyridin-3-yl)-1H,3H-pyrrolo[1,2-c]thiazole hydrochloride is prepared as in Example 11.

EXAMPLE 30

7-Chloroformyl-3-(pyridin-3-yl)-1H,3H-pyrrolo[1,2-c]thiazole hydrochloride (3.8 g) is added in small portions at a time, in the course of 15 minutes, at a temperature of between 21 and 26° C., to a solution of 4-methoxyaniline (3.1 g) and triethylamine (5.1 g) in 1,2-dichloroethane (50 cc). The suspension obtained is stirred at a temperature of the order of 20° C. for 16 hours. Methylene chloride (300 cc) and distilled water (100 cc) are then added to the reaction mixture. The aqueous phase is discarded and the organic phase is washed twice with distilled water (200 cc in total), 3 times with an N aqueous solution of sodium hydroxide (240 cc in total) and 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (5.3 g). This product is dissolved in boiling isopropanol (35 cc). The solution obtained is treated with decolourising charcoal (0.5 g) and filtered hot. The filtrate is cooled at a temperature of the order 4° C. for 1 hour. The crystals which have aopeared are filtered off, washed 3 times with isopropanol cooled to a temperature of the order 4° C. (15 cc in total) and 3 times with isopropyl ether (30 cc in total) and then dried under reduced pressure (20 mm Hg; 2.7 kPa) at a temperature of the order of 20° C., in the oresence of potassium hydroxide pellets. This gives N-(4-methoxyphenyl)-3-(pyridin-3-yl)-1H,3H-pyrrolo[1,2-c]thiazole-7-carboxamide (1.7 g) in the form of cream crystals melting at 120° C.

The 7-chloroformyl-3-(pyridin-3-yl)-1H,3H-pyrrolo[1,2-c]thiazole hydrochloride is prepared as in Example 11.

EXAMPLE 31

7-Chloroformyl-3-(pyridin-3-yl)-1H,3H-pyrrolo[1,2-c]thiazole hydrochloride (3.8 g) is added in small portions at a time, in the course of 15 minutes, at a temperature of between 22° and 28° C., to a solution of 3-chloroaniline (3.2 g) and triethylamine (5.1 g) in 1,2-dichloroethane (50 cc). The suspension obtained is stirred at a temperature of the order of 20° C. for 16 hours. 1,2-Dichloroethane (300 cc) and distilled water (100 cc) are then added to the reaction mixture. The aqueous phase is discarded and the organic phase is washed 3 times with distilled water (300 cc in total), 3 times with an N aqueous solution of sodium hydroxide (240 cc in total) and then 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (5.5 g) which is chromatographed on a column of diameter 6 cm, containing silica (0.04–0.063 mm) (480 g). Elution is carried out with pure ethyl acetale under a pressure of 0.5 bar (51 kPa), 100 cc fractions being collected. The first 11 fractions are discarded and the next 8 fractions are combined and concentrated to dryness under reduced pressure (20 mm Hg; 2.7 kPa) at a temperature of the order of 50° C. This gives a product (3.5 g), which is dissolved in boiling isopropanol (25 cc). The solution obtained is treated with decolourising charcoal (0.5 g) and filtered hot. The filtrate is cooled at a temperature of the order of 4° C. for 1 hour. The crystals which have appeared are filtered off, washed twice with isopropanol cooled to a temperature of the order of 4° C. (10 cc in total) and 3 times with isopropyl ether (15 cc in total) and then dried under reduced pressure (20 mm Hg; 2.7 kPa) at a temperature of the order of 20° C., in the presence of potassium hydroxide pellets. This gives N-(3-chlorophenyl)-3-(pyridin-3-yl)-1H,3H-pyrrolo[1,2-c]thiazole-7-carboxamide (2.2 g) in the form of cream crystals melting at 150° C.

The 7-chloroformyl-3-(pyridin-3-yl)-1H,3H-pyrrolo[1,2-c]thiazole hydrochloride is prepared as in Example 11.

EXAMPLE 32

7-Chloroformyl-3-(pyridin-3-yl)-1H,3H-pyrrolo[1,2-c]thiazole hydrochloride (3.8 g) is added in small portions at a time, in the course of 15 minutes, at a temperature of between 21 and 27° C., to a solution of o-toluidine (2.7 g) and triethylamine (5.1 g) in 1,2-dichloroethane (50 cc). The suspension obtained is stirred at a temperature of the order of 20° C. for 3 days. 1,2-Dichloroethane (300 cc) and distilled water (100 cc) are then added to the reaction mixture. The aqueous phase is discarded and the organic phase is washed twice with distilled water (200 cc in total), 3 times with an N aqueous solution of sodium hydroxide (240 cc in total) and 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (4.6 g), which is chromatographed on a column of diameter 6 cm, containing silica (0.04–0.063 mm) (480 g). Elution is carried out with pure ethyl acetate under a pressure of 0.5 bar (51 kPa), 100 cc fractions being collected. The first 15 fractions are discarded and the next 12 fractions are combined and concentrated to dryness under reduced pressure (20 mm Hg; 2.7 kPa) at a temperature of the order of 50° C. This gives a crude product (2.9 g) melting at 85° C. This product is dissolved in boiling isopropanol (25 cc). The solution obtained is treated with decolourising charcoal (0.5 g) and filtered hot. The filtrate is cooled at a temperature of. the order of 4° C. for 1 hour. The crystals which have appeared are filtered off, washed twice with isopropanol cooled to a temperature of the order of 4° C. (10 cc in total) and 3 times with isopropyl ether (15 cc in total) and then dried under reduced pressure (20 mm Hg; 2.7 kPa) at a temperature of the order of 20° C., in the presence of potassium hydroxide pellets. This gives N-(o-tolyl)-3-(pyridin-3-yl)-1H,3H-pyrrolo[1,2-c]thiazole-7-carboxamide (1.8 g) in the form of cream crystals melting at 101° C.

The 7-chloroformyl-3-(pyridin-3-yl)-1H,3H-pyrrolo[1,2-c]thiazole hydrochloride is prepared as in Example 11.

EXAMPLE 33

7-Chloroformyl-1H,3H-pyrrolo[1,2-c]thiazole hydrochloride (4.8 g) is added in small portions at a time, in the course of 15 minutes, at a temperature of between 21 and 28° C., to a suspension of N,N-dimethyl-p-phenylenediamine dihydrochloride (6.7 g) and triethylamine (13.1 g) in 1,2-dichloroethane (150 cc). The suspension obtained is stirred at a temperature of the order of 20° C. for 16 hours. 1,2-Dichloroethane (300 cc) and distilled water (100 cc) are added to the reaction mixture. The aqueous phase is discarded and the organic phase is washed twice with distilled water (200 cc in total), twice with an N aoueous solution of sodium hydroxide (200 cc in total) and 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (6.8 g), which is dissolved in boiling acetonitrile (90 cc). The solution obtained is treated with decolourising charcoal (0.5 g) and filtered hot. The filtrate is cooled at a temperature of the order of 4° C. for 1 hour. The crystals which have appeared are filtered off, washed 3 times with acetonitrile cooled to a temperature of the order of 4° C. (30 cc in total) and dried under reduced pressure (20 mm Hg; 2.7 kPa) at a temperature of the order of 20° C., in the presence of potassium hydroxide pellets. This gives N-(4-N',N'-dimethylaminophenyl)-3-(pyridin-3-yl)-1H,3H-pyrrolo[1,2-c]thiazole-7-carboxamide (3 g) in the form of beige crystals melting at 196° C.

The 7-chloroformyl-3-(pyridin-3-yl)-1H,3H-pyrrolo[1,2-c]thiazole hydrochloride is prepared as in Example 11.

EXAMPLE 34

A solution of 3-(pyridin-3-yl)-1H,3H-pyrrolo[1,2-c]thiazole-7-carboxylic acid (2 g) and N,N'-carbonyldiimidazole (2.1 g) in anhydrous tetrahydrofuran (50 cc) is stirred under dry nitrogen for 2 hours 30 minutes at a temperature of the order of 20° C. A solution of 1-(4-methoxyohenyl)-pioerazine (2.9 g) in anhydrous tetrahydrofuran (50 cc) is added to the solution obtained in the course of 10 minutes, at a temperature of between 20° C. and 25° C. The solution obtained is stirred at a temperature of the order of 20° C. for 16 hours. Distilled water (30 cc) is then added to the reaction mixture and the solvent is evaporated off under reduced pressure (20 mm Hg; 2.7 kPa) at a temperature of the order of 50° C. The oily residue obtained is taken up in distilled water (80 cc) and extracted 3 times with ethyl acetate (200 cc in total). The organic extracts are combined, washed 3 times with distilled water (240 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (4.5 g), which is dissolved in a boiling mixture of cyclohexane and ethyl acetate (50/50 by volume) (45 cc). The solution obtained is treated with decolourising charcoal (0.5 g) and filtered hot. The filtrate is cooled at a temperature of the order of 4° C. for 1 hour. The crystals which have appeared are filtered off, washed twice with a mixture of cyclohexane and ethyl acetate (50/50 by volume) (10 cc in total) and dried under reduced pressure (20 mm Hg; 2.7 kPa) at a temperature of the order of 20° C., in the presence of potassium hydroxide pellets. This gives 7-[4-(4-methoxyphenyl)-piperazin-1-yl-carbonyl]-3-(pyridin-3-yl)-1H,3H-pyrrolo[1,2-c]thiazole (2.1 g) in the form of cream crystals melting at 131° C.

The 3-(pyridin-3-yl)-1H,3H-pyrrolo[1,2-c]thiazole-7-carboxylic acid can be prepared as in Example 2.

EXAMPLE 35

A solution of 3-(pyridin-3-yl)-1H,3H-pyrrolo[1,2-c]thiazole-7-carboxylic acid (4.9.g) and N,N'-carbonyldimidazole (4.9 g) in anhydrous tetrahydrofuran (80 cc) is stirred under dry nitrogen for 2 hours at a temperature of the order of 25° C. and a solution of 4-methylpiperazine (3 g) in anhydrous tetrahydrofuran (20 cc) is then added in the course of 5 minutes, at a temperature of between 25° C. and 29° C. The solution obtained is stirred at a temperature of the order 20° C. for 16 hours and is then filtered, and the filtrate is concentrated to dryness under reduced pressure (20 mm Hg; 2.7 kPa) at a temperature of the order of 45° C. The crude oily residue obtained is chromatographed on a column of diameter 6 cm, containing silica (0.04–0.063 mm) (480 g). Elution is carried out with a mixture of methylene chloride and methanol (90/10 by volume) under a pressure of 0.5 bar (51 kPa), 100 cc fractions being collected. The first 12 fractions are discarded and the next 3 fractions are combined and concentrated to dryness under reduced pressure (20 mm Hg; 2.7 kPa) at a temperature of the order of 45° C. This gives a crude product (3.7 g), which is dissolved in ethanol (20 cc). A 5 N ethanolic solution of hydrogen chloride (7 cc) and then diethyl ether (140 cc) are added to the solution obtained. The suoernatant liquid is discarded and the oily precipitate is dissolved in a 5 N ethanolic solution of hydrogen chloride (60 cc) at a temperature of the order of 50° C. The solution obtained is cooled at a temperature of the order of 4° C. for 1 hour. The crystals which have appeared are filtered off, washed twice with ethanol (10 cc in total) and 3 times with diethyl ether (60 cc in total) and then dried under reduced pressure (20 mm Hg; 2.7 kPa) at a temperature of the order of 40° C., in the presence of potassium hydroxide pellets. This gives a product (2.65 g) melting at 170° C. This product (2.4 g) is suspended in a 4.5 N ethanolic solution of hydrogen chloride (12 cc). The suspension obtained is stirred at a temperature of the order of 20° C. for 30 minutes. The crystals are filtered off, washed twice with ethanol (6 cc in total) and 4 times with diethyl ether (40 cc in total) and then dried under reduced pressure (20 mm Hg; 2.7 kPa) at a temperature of the order of 20° C., in the presence of potassium hydroxide pellets. This gives 7-[(4-methylpiperazin-1-yl)-carbonyl]3-(pyridin-3-yl)-1H,3H-pyrrolo[1,2-c]thiazole as the trihydrochloride (2.7 g) in the form of white crystals melting at 161° C.

The 3-(pyridin-3-yl)-1H,3H-pyrrolo[1,2-c]thiazole-7-carboxylic acid can be prepared as in Example 2.

The present invention also provides pharmaceutical compositions comprising a compound of formula I, in the free form or in the form of an addition salt with a pharmaceutically acceptable acid or base, in association with a compatible pharmaceutically acceptable carrier (a term which, as used herein, includes, inter alia, coatings and adjuvents) which can be inert or physiologically active. The compositions can be administered orally, parenterally, rectally or topically.

Tablets, pills, powders (in particular in gelatine capsules or in cachets) or granules can be used as solid compositions for oral administration. In these compositions, the active compound of the invention may be mixed with one or more inert diluents such as starch, cellulose, sucrose, lactose or silica. These compositions can also comprise substances other than diluents, e.g. one or more lubricants such as magnesium stearate or talc, a colourant, a coating (coated tablets) or a lacquer.

Solution, suspensions, emulsions, syrups and pharmaceutically acceptable elixirs containing inert diluents such as water, ethanol, glycerol, vegetable oils or paraffin oil, are suitable forms of liquid compositions for oral administration. These compositions can also comprise substances other than diluents, e.g. wetting, sweetening, thickening, flavouring or stabilising agents.

Sterile compositions for parenteral administration are preferably suspensions, emulsions or aqueous or non-aqueous solutions. Water, propylene glycol, a polyethylene glycol, vegetable oils, in particular olive oil, injectable organic esters, e.g. ethyl oleate, or other suitable organic solvents can be used as the solvent or vehicle.

These compositions can also contain adjuvants, in particular wetting agents, agents for imparting isotonicity, emulsifiers, dispersants and stabilisers. Sterilisation can be carried out in several ways, e.g. by filtration under aseptic conditions, by incorporating sterilising agents into the composition, by irradiation or by heating. The compositions can also be prepared in the form of sterile solid compositions which can be dissolved in an injectable sterile medium at the time of use.

Compositions for rectal administration may be suppositories or rectal capsules, which, in addition to the active ingredient, may contain excipients such as cocoa butter, semi-synthetic glycerides or polyethylene glycols.

Compositions for topical administration can be, e.g., creams, ointments, lotions, eye lotions, mouthwashes, nose drops or aerosols.

In human therapy, the compounds of the invention are particularly useful in the treatment of allergic and inflammatory complaints and, in general, of any complaints in which the physio-pathological role of P.A.F.-Ac ether can be incriminated.

The dosage used depends on the desired effect and the duration of the treatment. For an adult, an appropriate dosage is generally between 25 and 100 mg per day, administered orally, intravenously or by inhalation in one or more individual doses.

In general, the physician will determine the posology which he considers to be most appropriate as a function of the age, the weight and all the other factors peculiar to the subject to be treated.

The Examples which follow illustrate compositions according to the invention.

EXAMPLE A

Tablets containing 25 mg doses of active ingredient and having the following composition are prepared by the usual technique:

| | |
|---|---|
| N—pyridin-2-yl-3-(pyridin-3-yl)-1H,3H—pyrrolo[1,2-c]thiazole-7-carboxamide | 25 mg |
| starch | 60 mg |
| lactose | 50 mg |
| magnesium stearate | 2 mg |

EXAMPLE B

An injectable solution containing 5 mg of active ingredient and having the following composition is prepared by the usual technique:

| | |
|---|---|
| 3-(pyridin-3-yl)-1H,3H—pyrrolo[1,2-c]thiazole-7-carboxamide | 5 mg |
| 0.1 N solution of hydrochloric acid | 0.2 cc |
| injectable solution q.s. | 2 cc |

We claim:
1. A 1H,3H-pyrrolo[1,2-c]-thiazole of the formula:

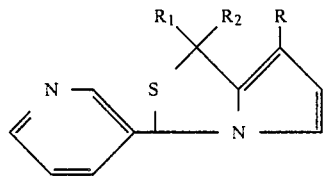

in which $R_1$ and $R_2$, which are identical or different, represent a hydrogen atom or an alkyl radical and
(a) R represents a
(1) cyano or
(2) alkylcarbonyl radical, or
(b) R represents
(3) a radical of the formula:

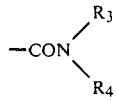

in which (3.1) $R_3$ represents a hydrogen atom and $R_4$ represents an amino, alkylamino, dialkylamino, phenylamino or diphenylamino radical, or
(3.2) $R_3$ and $R_4$, which are identical or different, represent a hydrogen atom, an alkyl radical of 1 to 5 carbon atoms or an unsubstituted or substituted phenyl radical, or
(3.3) $R_3$ represents a hydrogen atom and $R_4$ represents a
(3.3.1) pyridyl radical or
(3.3.2) an alkyl radical of 1 to 5 carbon atoms, which is substituted by a
(3.3.2.1) carboxyl, amino, alkylamino, dialkylamino,
(3.3.2.2) morpholino,
(3.3.2.3) piperidino or
(3.3.2.4) pyrrolidin-1-yl radical,
(3.3.2.5) a piperazin-1-yl radical (unsubstituted or substituted in the 4-position by an alkyl radical, a pyridyl radical, an unsubstituted or substituted phenyl radical or an unsubstituted or substituted benzyl radical), an
(3.3.2.6) unsubstituted or substituted phenyl radical or a
(3.3.2.7) pyridyl or
(3.3.2.8) imidazolyl radical, or
(3.4) $R_3$ and $R_4$ together with the nitrogen to which they are attached form an
(3.4.1) imidazolyl radical or
(3.4.2) a 5-membered or 6-membered heterocycle which can also contain another heteroatom such as oxygen, sulphur or nitrogen and which is
(3.4.2.1) unsubstituted or substituted by an alkyl, alkoxycarbonyl, hydroxyalkyl, aminoalkyl, alkylaminoalkyl, dialkylaminoalkyl,
(3.4.2.2) pyridyl,
(3.4.2.3) pyrimidinyl or
(3.4.2.4) pyrazinyl radical,
(3.4.2.5) an unsubstituted or substituted phenyl radical or an unsubstituted or substituted benzyl radical, or
(c) R represents
(4) a radical of the formula:

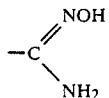

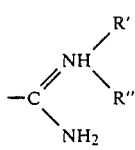

in which R' and R", which are identical or different, represent an alkyl radical, the alkyl radicals and alkyl portions in the above mentioned radicals being straight-chain or branched-chain and containing, unless mentioned otherwise, 1 to 4 carbon atoms, the possible substituents on the said phenyl and benzyl radicals being halogen, alkyl, alkoxy, alkylthio, trifluoromethyl or dialkylamino radicals, including the tautomeric forms of compounds of formula I when R represents a radical of the formula (III) or (IV), and its addition salts with acids and, where they exist, its metal salts and its addition salts with nitrogen bases.

2. A compound as claimed in claim 1, wherein in formula I, $R_1$ and $R_2$ both represent a hydrogen atom or an alkyl radical and
   (a) R represents a cyano or alkylcarbonyl radical, or
   (b) R represents a radical of the formula (II) in which $R_3$ represents a hydrogen atom and $R_4$ represents an amino radical, or $R_3$ and $R_4$, which are identical or different, represent a hydrogen atom or a pyridyl radical, an alkyl radical or a phenyl radical which is unsubstituted or substituted by halogen, alkyl, alkoxy or dimethylamino, or $R_3$ represents a hydrogen atom and $R_4$ represents alkyl of 1 to 5 carbon atoms, which is substituted by a carboxyl, dialkylamino or piperidino radical, a piperazin-1-yl radical substituted in the 4-position by a pyridyl radical, or a phenyl or imidazolyl radical, or $R_3$ and $R_4$ together with the nitrogen to which they are attached form an imidazolyl ring or a piperazinyl ring substituted in the 4-position by a hydroxyalkyl, pyridyl or pyrimidyl radical, a phenyl radical unsubstituted or substituted by an alkoxy radical or a benzyl radical, or
   (c) R represents a radical of the formula (III) or (IV) in which R' and R'', which are identical, represent an alkyl radical.

3. A compound as claimed in claim 1, wherein, in formula I, $R_1$ and $R_2$ both represent a hydrogen atom and R represents a radical of the formula (II) in which $R_3$ and $R_4$, which are identical or different, represent a hydrogen atom or an alkyl or phenyl radical, or $R_3$ represents a hydrogen atom and $R_4$ represents a pyridyl radical or an alkyl radical substituted by a phenyl or imidazolyl radical, or $R_3$ and $R_4$ together form a piperazinyl ring substituted in the 4-position by a pyridyl, phenyl or benzyl radical.

4. A compound as claimed in claim 1 which is N-pyridin-2-yl-3-(pyridin-3-yl)-1H,3H-pyrrolo[1,2-c]thiazole-7-carboxamide and its pharmaceutically acceptable acid addition salts.

5. A compound as claimed in claim 1 which is N-phenyl-3-(pyridin-3-yl)-1H,3H-pyrrolo[1,2-c]thiazole-7-carboxamide and its pharmaceutically acceptable acid addition salts.

6. A compound as claimed in claim 1 which is 3-(pyridin-3-yl)-1H,3H-pyrrolo[1,2-c]thiazole-7-carboxamide and its pharmaceutically acceptable acid addition salts.

7. A compound as claimed in claim 1 which is N-pyridin 3-yl-3-(pyridin-3-yl)-1H,3H-pyrrolo[1,2-c]thiazole-7-carboxamide and its pharmaceutically acceptable acid addition salts.

8. A compound as claimed in claim 1 which is N-methyl-3-(pyridin-3-yl-1H,3H-pyrrolo[1,2-c]thiazole-7-carboxamide and its pharmaceutically acceptable acid addition salts.

9. A compound as claimed in claim 1 which is N-butyl-3-(pyridin-3-yl)-1H,3H-pyrrolo[1,2-c]thiazole-7 carboxamide and its pharmaceutically acceptable acid addition salts.

10. A compound as claimed in claim 1 which is N-benzyl-3-(pyridin-3 yl)-1H,3H-pyrrolo-[1,2-c]thiazole-7-carboxamide and its -pharmaceutically acceptable acid addition salts.

11. A compound as claimed in claim 1 which is N-[2-(i-midazol-4 -yl)-ethyl]3-(pyridin-3-yl)-1H,3H-pyrrolo[1,2-c]thiazole-7-carboxamide and its pharmaceutically acceptable acid addition salts.

12. A compound as claimed in claim 1 which is (4-phenylpiperazin-1-yl)-7-carbonyl-3-(pyridin-3-yl)-1H,3H-pyrrolo[1,2-c]thiazole and its pharmaceutically acceptable acid addition salts.

13. A compound as claimed in claim 1 which is [4-(pyridin-2-yl)-piperazin-1 yl]-7 carbonyl-3-(pyridin-3-yl)-1H,3H -pyrrolo[1,2-c]thiazole and its pharaaceutically acceptable acid addition salts.

14. A compound as claimed in claim 1 which is (4-benzylpiperazin 1-yl)-7-carbonyl 3-(pyridin-3-yl)-1H,3H-pyrrolo[1,2-c]thiazole and its pharmaceutically acceptable acid addition salts.

15. A pharmaceutical composition comprising a compound according to claim 1 in the free form or in the form of an addition salt with a pharmaceutically acceptable acid or base in association with a compatible, pharmaceutically acceptable carrier.

16. A method for the prophylactic or therapeutic treatment of allergic or inflammatory complaints which comprises administering to a subject in need of such treatment an effective amount of a compound according to claim 1 in the free form or in the form of an addition salt with a pharmaceutically acceptable acid or base.

* * * * *